United States Patent [19]
Kamb

[11] Patent Number: 5,998,136
[45] Date of Patent: Dec. 7, 1999

[54] SELECTION SYSTEMS AND METHODS FOR IDENTIFYING GENES AND GENE PRODUCTS INVOLVED IN CELL PROLIFERATION

[75] Inventor: Carl Alexander Kamb, Salt Lake City, Utah

[73] Assignee: Arcaris, Inc., Salt Lake City, Utah

[21] Appl. No.: 08/699,266

[22] Filed: Aug. 19, 1996

[51] Int. Cl.[6] .............................. C12Q 1/68; C12Q 1/70; C12Q 1/02

[52] U.S. Cl. .................................... 435/6; 435/5; 435/29; 435/34

[58] Field of Search ................................ 345/5, 6, 29, 34

[56] References Cited

U.S. PATENT DOCUMENTS

| | | | |
|---|---|---|---|
| 5,382,510 | 1/1995 | Levine et al. .............................. | 435/6 |
| 5,811,234 | 9/1998 | Roninson et al. .......................... | 435/6 |

OTHER PUBLICATIONS

Li et al, "Isolation of ORC6, a component of the yeast origin recognition complex by a one–hybrid system", Science 262:1870–1874, Dec. 1993.

Knippschild et al, "Abrogation of wild–type p53 mediated growth inhibition by nuclear exclusion", Oncogene 12:1755–1765, Apr. 1996.

Muthukkumar et al, "Role of EGR–1 in thapsigargin inducible apoptosis in the melanoma cell line A375–C6", Mol. Cell. Biol. 15(11):6262–6272, Nov. 1995.

Bani et al, "Multiple features of advanced melanoma recapitulated in tumorigenic variants of early stage (radial growth phase) human melanoma cell lines: evidence for a dominant phenotype", Cancer Res. 56:3075–3086, Jul. 1996.

Abrahamson et al., 1995, "Regulation of p53–Mediated Apoptosis and Cell Cycle Arrest by Steel Factor", Mol. Cell. Biol. 15:6953–6960.

Arsura et al., 1995, "Variant Max Protein, Derived by Alternative Splicing, Associates with c–Myc In Vivo and Inhibits Transactivation", Mol. Cell. Biol. 15:6702–6709.

Bartel et al., 1995, "Analyzing Protein–Protein Interactions Using Two–Hybrid System", Methods Enzynol. 254:241–263.

Bishop, J.M. 1983, "Cellular Oncogenes and Retroviruses", Annu. Rev. Biochem. 52:301–354.

Bishop, J.M. 1987, "The Molecular Genetics of Cancer", Science 235:305–311.

Bourgeois et al, 1993, "Expression of an mdr Gene is Associated with a New Form of Resistance to Dexamethasone–Induced Apoptosis", Mol. Endocrinol. 7:840–851.

Cannon–Albright et al., 1992, "Assignment of a Locus for Familial Melanoma, MLM, to Chromosome 9p13–p22", Science 258:1148–1152.

Cavenee et al., 1983, "Expression of Recessive Alleles by Chromosomal Mechanisms in Retinoblastoma", Nature 305:779–784.

Chen et al., 1996, "Activation and Inhbition of the AP–1 Complex in Human Breast Cancer Cells", Mol. Carcinog. 15:215–226.

Cho et al., 1976, "Revertants of Human Cells Transformed by Murine Sarcoma Virus", Science 194:951–953.

Collins and Rivas, 1993, "The Control of Apoptosis in Mammalian Cells", TIBS 18:307–308.

Copeland et al., 1979, "Transformation of NIH/3T3 Mousel Cells by DNA of Rous Sarcoma Virus", Cell 17:993–1002.

Daub et al., 1996, "Role of Transactivation of the EGF Receptor in Signalling by G–protein–coupled Receptors", Nature 379:557–560.

Denko et al. 1995, "Mitotic and Post Mitotic Consequences of Genomic Instability Induced by Oncogenic Ha–Ras", Somat. Cell. Mol. Genet. 21:241–253.

Egawa et al., 1995, "Early Detection of Prostate Cancer", Cancer 76:463–472.

Evan et al., 1992, "Induction of APoptosis in FIbroblasts in c–myc Protein", Cell 69:119–128.

Fieck et al., 1992, "Modifications of the E.coli Lac Repressor for Expression in Eukaryotic Cells: Effects of Nuclear Signal Sequences on Protein Activity and Nuclear Accumulation", Nucleic Acid Res. 20:1785–1791.

Fischinger et al., 1972, "Reversion of Murine Sarcoma Virus Transformed Mouse Cells: Variants without a Rescuable Sarcoma Virus", Science 176:1033–1035.

Francke et al., 1976, "Retinoblastoma and Chromosome 13", Cytogenet. Cell Genet. 16:131–134.

Francke et al., 1979, "Aniridia–Wilms' Tumor Association: evidence for Specific Deletion of 11p13", Cytogenet. Cell Genet. 24:185–192.

Friend et al., 1986, "A Human DNA Segment with Properties of the Gene that Predisposes to Retinoblastoma and Osteosarcoma", Nature 343:643–646.

Friend et al., 1987, "Deletions of a DNA Sequence in Retinoblastomas and Mesenchymal Tumors: Organization of the Sequence and its Encoded Protein", Proc. Natl. Acad. Sci. U.S.A. 84:9059–9063.

(List continued on next page.)

Primary Examiner—Jeffrey Fredman
Attorney, Agent, or Firm—Fish & Neave; James F. Haley, Jr.; Barbara A. Ruskin

[57] ABSTRACT

The present invention is directed to selection systems for the identification of cell proliferation genes based on functional analysis. More specifically, the invention is directed to a process for the identification of a cell proliferation promoting activity, the isolation of genes involved in such cell proliferation promoting activity, and the use of the so identified genes for the diagnosis or treatment of a disease associated with excessive cell proliferation. The invention further is directed to the design and development of antibodies, peptides, nucleic acids, and other compounds which specifically interfere with the function of the identified gene and/or its gene product, and pharmaceutical compositions comprising such compounds, for the treatment of diseases associated with inappropriate or unregulated cell proliferation.

28 Claims, 6 Drawing Sheets

OTHER PUBLICATIONS

Gaits et al., 1995, "Increase in Receptor–like Protein Tyrosine Phosphatase Activity and Expression Level on Density–dependent Growth Arrest of Endothelial Cells", Biochem. J. 311:97–103.

Galiana et al., 1995, "Indentification of a Neural–specific cDNA, NPDC–1, able to Down–regulate cell Proliferation and to Suppress Transformation", Proc. Natl. Acad. Sci. U.S.A. 92:1560–1564.

Gessler et al., 1990, "Homozyous Deletion in Wilms Turmors of a Zinc–finger Gene Identified by Chromosome Jumping", Nature 343:774–778.

Gossen and Bujard, 1992, "Tight Control of Gene Expression in Mammalian Cells by Tetracycline–responsive Promoters", Proc. Natl. Acad. Sci. U.S.A. 89:5547–5551.

Greenberger and Aaronson, 1974, "Morphologic Revertants of Murine Sarcoma Virus Transformed Nonproducer BALB/3T3: Selective Techniques for Isolation and Biologic Properties in Vitro and In VIvo", Virology 57:336–346.

Hall et al., 1990, "Linkage of Early–Onset Familial Breast Cancer to Chromosome 17q21", Science 250:1684–1689.

Harbour et al., 1988, "Abnormalities in Structure and Expression of the Human Retinoblastoma Gene in SCLC", Science 241:353–357.

Harrington et al., 1994, "Oncogenes and Cell Death", Curr. Opin. Genet. Dev. 4:120–129.

Haslinger et al., 1985, "Upstream Promoter Element of the Human Metallothionein–11A Gene Can Act Like an Enhancer Element", Proc. Natl. Acad. Sci. U.S.A. 82:8572–8576.

Holt et al., 1996, "Growth Retardation and Tumour Inhibition by BRCA1", Nat. Genet. 12:298–302.

Horuk et al., 1993, "Purification, Receptor Binding Analysis, and Biiological Characterization of Human Melanoma Growth Stimulating Activity (MGSA)", J. Biol. Chem. 268:541–546.

Huang et al., 1988, "Suppression of the Neoplastic Phenotype by Replacement of the RB Gene in Human Cancer Cells", Science 242:1563–1566.

Inoue et al., 1983, "Rat Mutant Cells Showing Temperature Sensitivity for Transformation by WIld–type Moloney Murine Sarcoma Virus", Virology 125:242–245.

Itoh et al., 1991, "The polypeptide Encoded by the cDNA for Human Cell Surface Antigen Fas Can Mediate Apoptosis", Cell 66:233–243.

Johnson et al., 1995, "Selective Tumorigenesis in Nonparenchymal Liver Epithelial Cell Lines by Hepatocyte Growth Factor Transfection", Cancer Lett. 96:37–48.

Kamb et al., 1994, "A Cell Cycle Regulator Potentially Involved in Genesis of Many Tumor Types", Science 264:436–440.

Kashles et al., 1991, "A Dominant Negative Mutation Suppresses the Function of Normal Epidermal Growth Factor Receptors by Heterodimerization", Mol. Cell. Biol. 11:1454–1463.

Korsymeyer, 1992, "Bcl–2: A recpressor of Lymphocyte Death", Immunol. Today 13:285–288.

Kruglyak et al., 1995, "Complete Multipoint Sib–Pair Analysis of Qualitative and Quantitative Traits", Am. J. Hum. Genet. 57:439–454.

Kruglyak et al., 1995, "High–resolution Genetic Mapping of Complex Traits", Am. J. Hum. Genet. 56:1212–1223.

Kyprianou et al., 1991, "Programmed Cell Death During Regression of the MCF–7 Human Breast Cancer Following Estrogen Ablation", Cancer Res. 51:162–166.

Land et al., 1983, "Tumorigenic Conversion of Primary Embryo Fibrolblasts Requires at Least Two Cooperating Oncogenes", Nature 304:596–602.

Latif et al., 1993, "Identification of the von Hippel–Lindau Disease Tumor Suppressor Gene", Science 260:1317–1320.

Lee et al., 1987, "The Retinoblastoma Susceptibility Gene Encodes a Nuclear Phosphoprotein Associated with DNA Binding Activity", Nature 329:642–645.

Lennon et al., 1996, "The I.M.A.G.E. Consortium: An Inegyrated Molecular Analysis of Genomes and Their Expression", Genomics 33:151–152.

Liang et al., 1995, "Analysis of ALtered Gene Expression by Differential Display", Methods Enzymol. 254:304–321.

Lin et al., 1992, "Growth Arrest Induced by Wild–type p53 Protein Blocks Cells Prior to or Near the Restriction Point in Late $G_1$ Phase", Proc. Natl. Acad. Sci. U.S.A. 89:9210–9214.

Lowe et al., 1994, "p53 Status of the Efficacy of Cancer Therapy in Vivo", Science 266:807–810.

Martin et al., 1994, "Dicing with Death: Dissecting the Components of the Apoptosis Machinery", TIBS 19:26–30.

Maruyama et al., 1981, "Characterization of Flat Revertant Cells Isolated from Simian Virus 40–Transformed Mouse and Rat Cells Which Contain Multiple Copies of Viral Genomes", J. Virol. 37:1028–1043.

Mathey–Prevot et al., 1984, "Revertants and Partial Transformants of Rat Fibroblasts Infected with Fujinami Sarcoma Virus", J. Virol. 50:325–334.

Mendelsohn and Brent, 1994, "Applications of Interaction Traps/Two–hybrid Systems to Biotechnology Research", Curr. Opin. Biotechnol. 5:482–486.

Mettlin et al., 1996, "The Results of a Five–year Early Prostate Cancer Detection Intervention", Cancer 77:150–159.

Miki et al., 1994, "A Strong Candidate for the Breast and Ovarian Cancer Susceptibility Gene BRCA1", Science 266:66–71.

Millauer et al., 1994, "Glioblastoma Growth Inhibited in vivo by a dominant–negative Flk–1 Mutant", Nature 367:576–579.

Nishisho et al., 1991, "Mutations of Chromosome 5q21 Genes in FAP and Colorectal Cancer Patients", Science 253:665–669.

Nobori et al., 1994, "Deletions of the Cyclin–dependent Kinase–4 Inhibitor Gene in Multiple Human Cancers", Nature 368:753–756.

Norton et al., 1984, "Expression of Kirsten Murine Sarcoma VIrus in Transformed Nonproducer and Revertant NIH/3T3 Cells: Evidence for Cell–mediated Resistance to a Viral Oncogene in Phenotypic Reversion", J. VIrol. 50:439–444.

Okazawa et al., 1996, "Bcl–2 Inhibits Retinoic Acid–induced Apoptosis During the Neural Differentiation of Embryonal Stem Cells", J. Cell Biol. 132:955–968.

Ozanne and Vogel, 1974, "Selection of Revertants of Kirsten Sarcoma Virus Transformed Nonproducer BALB/3T3 Cells", J. Virol. 14:239–248.

Partin et al., 1995, "Standard Versus Age–specific Prostate SPecific Antigen Reference Ranges Among Men with Clinically localized Prostate Cancer: A Pathology Analysis", J. Urol. 155:1336–1339.

Pickett et al., 1995, "Epidermal Growth Factor and Ras Regulate Gene Expression in GH4 Pituitary Cells by Separate, Antagonistic Signal Transduction Pathways", Mol. Cell. Biol. 15:6777–3784.

Redemann et al., 1992, "Anti–oncogenic Activity of Signalling–defective Epidermal Growth Factor Receptor Mutants", Mol. Cell. Biol. 12:491–498.

Rotter et al., 1993, "In Search of Functions of Normal p53 Protein", Trends ell. Biol. 3:46–49.

Rouleau et al., 1993, "Alteration in a New Gene Encoding a Putative Membrane–organizing Protein Causes Neuro–fibromatosis Type 2", Nature 363:515–521.

Ryan et al., 1985, "Isolation of a Simian Virus 40 T–Antigen–Positive, Transformation–Resistant Cell Line by Indirect Selection", Mol. Cell. Biol. 5:3577–3582.

Sacks et al., 1979, "Abelson Murine Leukemia VIrus–Infected Cell Lines Defective in Transformation", VIrology 97:231–240.

Schena et al., 1995, "Quantitative Monitoring of Gene Expression Patterns with a Complementary DNA Microarray", Science 270:467–470.

Schroder et al., 1995, "European Randomized Study of Screening for Prostate Cancer", Cancer 76:129–134.

Schumacher et al., 1994, "The Chicken Mx Promoter Contains an ISRE Motif and Confers Interferon Inducibility to a Reporter Gene in Chick and Monkey Cells", Virology 203:144–148.

Serrano et al., 1993, "A New Regulatory Motif in Cell–cycle Control Causing Specific Inhibition of Cyclin D/CDK4", Nature 366:704–707.

Shi et al., 1992, "Role for c–myc in Activation–Induced Apoptotic Cell Death in T Cell Hybridomas", Science 257:212–214.

Simonson et al., 1996, "Nuclear Signaling by Endothelin–1 Required Src Protein–tyrosine Kinases", J. Biol. Chem. 271:77–82.

Stehelin et al., 1976, "DNA Related to the Transforming Gene(s) of Avian Sarcoma VIruses is Present in Normal Avian DNA", Nature 260:170–173.

Steinberg et al., 1978, "Isolation and Characterization of T Antigen–Negative Revertants from a Line of Transformed Rat Cells Containing One Copy of the SV40 Genome,", Cell 13:19–32.

Stephenson et al., 1973, "Characterization of Morphologic Revertants of Murine and Avian Sarcoma Virus–Transformed Cells", J. Virol. 11:218–222.

Tavtigian et al., 1996, "The Complete BRCA2 Gene and Mutations in Chromosome 13q–linked Kindreds", Nature Genetics 12:1–6.

Valyi–Nagy et al., 1993, "Spontaneous and Induced Differentiation of Human Melanoma Cells", Int. J. Cancer 54:159–165.

van Weering et al., 1995, "Ret Receptor Tyrosine Kinase Activates Intracellular Signal–regulated Kinase 2 in SK–N–MC Cells", Oncogene 11:2207–2214.

Varmus et al., 1981, "Revertants of an ASV–Transformed Rat Cell Line Have Lost the Complete Provirus or Sustained Mutations in src", Virology 108:28–46.

Varmus et al., 1981, "Retroviruses as Mutagens: Insertion and Excision of a Nontransforming Proviruis Alter Expression of a Resident Transforming Provirus", Cell 25:23–26.

Velcich et al., 1995, "Patterns of Expression of Lineage–specific Markers During the in VItro–induced Differentiation of HT29 COlon Carcinoma Cells", Cell Growth Differ. 6:749–757.

Velculescu et al., 1995, "Serial Analysis of Gene Expression", Science 270:484–487.

Vito et al., 1996, "Interfering with Apoptosis: $Ca^{2+}$–Binding Protein ALG–2 and Alzheimer's Disease Gene ALG–3", Science 271:521–525.

Vogel and Pollack, 1974, "Isolation and Characterization of Revertant Cell Lines VI. SUsceptibility of Revertants to Retransformaation by Simian VIrus 40 and Murine Sarcoma Virus", J. Virol. 14:1404–1410.

Weinbert, 1994, "Oncogenes and Tumor Suppressor Genes", CA Cancer J. Clin. 44:160–170.

Wilson et al., 1986, "A Frameshift at a Mutational Hotspot in the Polyoma Virus Early Region Generates Two New Proteins that Defines T–Antigen Functional Domains", Cell 44:477–487.

Wolfel et al., 1995, "A $p16^{INK4a}$–Insensitive CDK4 Mutant Targeted by Cytolytic T Lymphocytes in a Human Melanoma", Science 269:1281–1284.

Wooster et al., 1993, "Identification of a Breast Cancer Susceptibility Gene BRAC2", Nature 378:789–792.

Wooster et al., 1994, "Localization of a Breast Cancer Susceptibility Gene, BRCA2, to Chromosome 13q12–13", Science 265:2088–2090.

Xie et al., 1995, "Dominant–negative Mutants of Grb2 Induced Reversal of the Transformed Phenotypes Caused by the Point Mutation–activated Rat HER–2/Neu", J. Biol Chem. 270:30717–30724.

Xiong et al., 1993, "p21 is A Universal Inhibitor to Cyclin Kinases", Nature 366:701–704.

Xu et al., 1990, "The Neurofibromatosis Type 1 Gene Encodes a Protein Related to GAP", Cell 62:599–608.

Yokota et al., 1988, "Altered Expression of the Retinoblastoma (RB) Gene in Small–cell Carcinoma of the Lung", Oncogene 3:471–475.

Zarbl et al., 1991, "Functional In Vitro Assays for the Isolation of Cell Transformation Effector and Suppressor Genes", Environmental Health Perspectives 93:83–89.

Zeigler et al., 1994, "Sunburn and p53 in the Onset of Skin Cancer", Nature 372:773–776.

1 Introduce P16 expression vector into cells

2 Induce p16 expression

3 Select growth-proficient reverants

4 Characterize genetic changes

1 Introduce perturbagen library into cells

2 Select growth-proficient reverants

3 PCR amplify resident perturbagens

4 Determine perturbagen DNA sequence

AGGCAACAGCTACC...

rev 1

2

3

4

5

6 pOP/p16+ pOP 5637 (Rb-)

rev 1 2 3 4 5 6

5637 (Rb-)

T24 (Rb+)

SELECTION SYSTEMS AND METHODS FOR IDENTIFYING GENES AND GENE PRODUCTS INVOLVED IN CELL PROLIFERATION

I. FIELD OF THE INVENTION

The present invention relates to selection systems for the identification of novel cell proliferation genes. More specifically, the invention relates to a process for the identification of cell proliferation promoting activity, the isolation of genes involved in such cell proliferation promoting activity, and the use of the so identified genes for the diagnosis or treatment of a disease related to aberrant or unregulated cell proliferation. The invention further relates to the design and development of antibodies, peptides, nucleic acids, and other compounds which specifically interfere with the function or regulation of the identified gene and/or its gene product, and pharmaceutical compositions comprising such compounds, for the targeted treatment of diseases related to aberrant or unregulated cell proliferation.

II. BACKGROUND OF THE INVENTION

General Background. In the past decade it has become apparent that many diseases result from genetic alterations in signaling pathways. These include diseases related to unregulated cell proliferation such as cancers, atherosclerosis and psoriasis as well as inflammatory conditions such as sepsis, rheumatoid arthritis and tissue rejection. The finding that these proliferative diseases are based on genetic defects refocused the medical community to seek new modalities for disease management which essentially consist of designing drugs which modulate cell signaling. In order to develop highly specific drugs, i.e., drugs which potently interfere with uncontrolled cell proliferation but have low toxicity or side effects, it is crucial to identify the genes encoding polypeptides involved in the cellular signal transduction pathways whose aberrant function may result in the loss of growth control.

Although tremendous progress in understanding relevant signal transduction pathways has been made in recent years, it is quite clear that many of the genes involved in the development of proliferative disorders, referred to herein generally as "cell proliferation genes", remain to be discovered.

Cell Proliferation Genes. Genes whose aberrant expression or function may contribute to cell proliferation disorders fall into two general categories: (1) dominant transforming genes, including oncogenes, and (2) recessive cell proliferation genes, including tumor suppressor genes and genes encoding products involved in programmed cell death ("apoptosis").

Oncogenes generally encode proteins that are associated with the promotion of cell growth. Because cell division is a crucial part of normal tissue development and continues to play an important role in tissue regeneration, oncogene activity, properly regulated, is essential for the survival of the organism. However, inappropriate expression or improperly controlled activation of oncogenes may drive uncontrolled cell proliferation and result in the development of severe diseases, such as cancer. Weinberg, 1994, *CA Cancer J. Clin.* 44:160–170.

Tumor suppressor genes, on the other hand, normally act as "brakes" on cell proliferation, thus opposing the activity of oncogenes. Accordingly, inactivation of tumor suppressor genes, e.g., through mutations or the removal of their growth inhibitory effects may result in the loss of growth control, and cell proliferative diseases such as cancer may develop. Weinberg, 1994, *CA Cancer J. Clin.* 44:160–170.

Related to tumor suppressor genes are genes whose product is involved in the control of apoptosis; rather than regulating proliferation of cells, they influence the survival of cells in the body. In normal cells, surveillance systems are believed to ensure that the growth regulatory mechanisms are intact; if abnormalities are detected, the surveillance system switches on a suicide program that culminates in apoptosis.

Several genes that are involved in the process of apoptosis have been described. See, for example, Collins and Lopez Rivas, 1993, *TIBS* 18:307–308; Martin et al., 1994, *TIBS* 19:26–30. Gene products which have been implicated in the control of or participation in apoptosis include bcl-2 (Korsymeyer, 1992, *Immunol. Today* 13:285–288), c-myc (Shi et al., 1992, *Science* 257:212–214; Evan et al., 1992, *Cell* 69:119–128), p53 (Rotter et al., 1993, *Trends Cell. Biol.* 3:46–49), TRPM-2/SGP (Kryprianou et al., 1991, *Cancer Res.* 51:162–166), and Fas/APO-1 (Itoh et al., 1991, *Cell* 66:233–243). Cells that are resistant to apoptosis have an advantage over normal cells, and tend to outgrow their normal counterparts and dominate the tissue. As a consequence, inactivation of genes involved in apoptosis may result in the progression of tumors, and, in fact, is an important step in tumorigenesis.

Mutations in tumor suppressor genes and genes encoding products involved in the control of apoptosis are typically recessive; i.e., both copies of the gene, the maternally inherited copy and the paternally inherited one, must be inactivated by mutation to remove the effect of the gene product. Usually, a single functional copy of such genes is sufficient to maintain tumor suppression. Predisposition to certain hereditary cancers involves mutant tumor suppressor genes. For example, if an individual inherits a single defective tumor suppressor gene from her father, initially her health will be uncompromised, since each cell still contains a functional copy of the gene inherited from her mother. However, as cells divide, mutations accumulate. Thus, at one point, the remaining normal copy in a cell may be inactivated by mutation to remove the function of the tumor suppressor, thereby completing one of the steps toward tumor formation. Such a cell may give rise to descendant cells which represent the early stages of cancer.

Of course, individuals who inherit a full normal complement of tumor suppressor genes can develop cancer as well. However, because two inactivating mutations are required, the development of the disease is much less frequent in such "normal" individuals, i.e., not predisposed to cancer.

Tumor suppressor genes and oncogenes participate in growth control pathways in normal cells in such a way that the appropriate level of cell division is maintained. Disruption of these pathways by mutation of the component genes, oncogenes or tumor suppressor genes, is the underlying cause of cancer. Growth control in complex organisms like humans is a very important and complicated process. Thus, multiple genetic pathways for growth control are involved. Some pathways operate in all cell types in the body. Other pathways are much more specific and function only in certain cells.

Discovery Of Cell Proliferation Genes. Oncogenes and tumor suppressor genes have traditionally been identified by different methods. However, each of the approaches currently employed for the identification and isolation of cell proliferation genes has limitations on the types of genes that can be retrieved.

A first approach involves the detection and identification of transforming retroviruses and chromosomal translocations in tumors, which has provided the means to identify dozens of oncogenes. Bishop, 1983, *Annu. Rev. Biochem.* 52:350–354; Stehelin et al., 1976, *Nature* 260:170–173; Bishop, 1987, *Science* 235:305–311. However, this strategy is largely limited to the identification of dominant oncogenes and it rarely leads to the identification of tumor suppressor genes since inappropriate tumor suppressor functions are recessive. Moreover, viral spread is not facilitated by decreased cell growth, thus it serves little purpose for viruses to transduce tumor suppressor genes. Similarly, viral insertion or chromosomal translocations are single events. Thus, dominant changes are far more likely to be manifested than recessive changes.

A second traditional method for identifying cell proliferation genes has been the genetic analysis of kindreds, followed by positional cloning. Kindred analysis is, in principle, suited both for the identification of oncogenes as well as recessive cell proliferation genes, including tumor suppressor genes and/or genes encoding products involved in the control of apoptosis. Through kindred analysis many recessive cell proliferation genes have been uncovered, including APC (Nishisho et al., 1991, *Science* 253:665–669), NFI (Xu et al., 1990, *Cell* 62:599–608), NF2 (Rouleau et al., 1993, *Nature* 363:515–521), RB (Friend et al., 1986, *Nature* 343:643–646), MLM (Cannon-Albright et al., 1992, *Science* 258:1148–1152; Kamb et al., 1994, *Science* 264:436–440), BRCA1 (Hall et al., 1990, *Science* 250:1684–1989; Miki et al., 1994, *Science* 266:66–71), BRCA2 (Wooster et al., 1994, *Science* 265:2088–2090; Wooster et al., 1995, *Nature* 378:789–792; Tavtigian et al., 1996, *Nature Genetics* 12:1–6), WT1 (Francke et al., 1979, *Cytogenet. Cell Genet.* 24:185–192; Gessler et al., 1990, *Nature* 343:774–778), and VHL (Latif et al., 1993, *Science* 260:1317–1320). However, a major disadvantage of the analysis of kindreds is that it is rather slow and limited, because the identification of cell proliferation genes depends on the existence of chance mutations that become established in the cell population, and cause an increased risk that is dramatic enough to be visible above the level of nonhereditary (sporadic) cancer in the population. Kruglyak et al., 1995, *Am. J. Hum. Genet.* 57:439–454; Kruglyak et al., 1995, *Am. J. Hum. Genet.* 56:1212–1223.

A third approach traditionally pursued to identify and isolate cell proliferation genes is the analysis of homozyous or hemizygous genetic lesions in tumor cells. These lesions include regions of loss of heterozygosity (LOH) or homozygous deletions. Horuk et al., 1993, *J. Biol. Chem.* 268:541–546.

Finally, a method which has been employed for isolating growth control genes of the tumor suppressor class involves the selection of variants that have lost certain malignancy traits, namely "revertants". Such revertant lines, however, are typically difficult to identify and separate from the majority of rapidly growing parental cells. Still, a number of such revertants have been isolated from populations of cells transformed by a variety of oncogenes and subsequent treatment with various cytotoxic agents which are toxic to growing cells or cancer cells. Fischinger et al., 1972, *Science* 176:1033–1035; Greenberger et al., 1974, *Virology* 57:336–346; Ozanne et al., 1974, *J. Virol.* 14:239–248; Vogel et al., 1974, *J. Virol.* 14:1404–1410; Cho et al., 1976, *Science* 194:951–953; Steinberg et al., 1978, *Cell* 13:19–32; Maruyama et al., 1981, *J. Virol.* 37:1028–1043; Varmus et al., 1981, *Cell* 25:23–26; Varmus et al., 1981, *Virology* 108:28–46; Mathey-Prevot et al., 1984, *J. Virol.* 50:325–334; Wilson et al., 1986, *Cell* 44:477–487; Stephenson et al., 1973, *J. Virol.* 11:218–222; Sacks et al., 1979, *Virology* 97:231–240; Inoue et al., 1983, *Virology* 125:242–245; Norton et al., 1984, *J. Virol.* 50:439–444; Ryan et al., 1985, *Mol. Cell. Biol.* 5:3477–3582. Usually, cells are exposed to these agents under such conditions where cells that have reacquired a non-transformed phenotype are contact inhibited, and hence, are less susceptible to these cytotoxic agents, leading to preferential elimination of the transformed parental cells and, after several cycles, the isolation of morphologic revertants.

In addition to being both inefficient and time consuming, the above described selection for tumor suppressor genes is based on differential growth parameters of normal versus transformed cells and hence may preclude the isolation of certain classes of revertants. Moreover, the selection procedure itself may induce epigenetic changes or changes in the number of chromosomes. Furthermore, if the cytotoxic agents used are themselves mutagenic, then their continuous presence during the selection period may generate a revertant phenotype resulting from multiple mutational events. While any of these mechanisms may result in the production of a revertant phenotype, the nature of these genetic or epigenetic changes may preclude their analysis by gene transfer experiments.

Obviously, the most constraining factor for the utility of tumor cells in gene discovery is the lack of powerful selection procedures allowing the identification of new genes. It is well recognized that there is a need for a rapid and efficient selection procedure that would permit the isolation of tumor cell revertants resulting from a single mutational event. With this objective, Zarbl et al. developed an alternative assay for the selection of revertant tumor cells. Zarbl et al., 1991, *Environmental Health Perspectives* 93:83–89. This selection protocol is based on the prolonged retention of a fluorescent molecule within the mitochondria of a number of transformed cells relative to non-transformed cells. Indeed, in a significant number of cases, retention of fluorescent molecules within mitochondria seems coupled to transformation. However, because the prolonged dye retention phenotype is neither essential nor sufficient for cell transformation, this approach is limited to some specific types of mechanisms of transformation.

Other methods which have been used to search for cell proliferation genes involve biochemical approaches underlying analysis of cell cycle regulators (Serrano et al., 1993, *Nature* 366:704–707; Xiong et al., 1993, *Nature* 366:701–704), random sequencing of expressed sequence tags (ESTs) and homology comparisons (Lennon et al., 1996, *Genomics* 33:151–152), and methods for identifying differentially expressed genes, such as differential display (Liang et al., 1995, *Methods Enzymol.* 254:304–321). None of these approaches, however, offers a way to directly assess the function of the genes. Instead, candidates are identified based on a presumed (or identifiable) biochemical function or on an abnormal pattern of expression. These candidates are then tested further for involvement in cancer. Such tests include either mutational alteration in primary cancers or cell lines, experiments using somatic cells (for example, to determine the effect of ectopic expression), or experiments in transgenic mice or knockout mice containing inactivated genes.

It is apparent that these selection methods have a number of drawbacks and limitations. Therefore it is desirable, and the objective of the present invention, to develop rapid and efficient selection procedures that would permit the identification and isolation of large numbers of novel genes, particularly cell proliferation genes, based on functional analysis. In accordance with its objective, the present invention provides efficient selection systems which permit the isolation of growth-proficient revertants resulting from a single mutational event in growth arrested cells.

III. SUMMARY OF INVENTION

The subject invention is directed to selection systems for the identification of cell proliferation genes based on functional analysis. Generally, the selection procedures of the subject invention involve the use of variants of transformed cells to identify a cell proliferation promoting activity.

The selection systems of the invention may include creation of growth arrested tumor cell lines or cells which may undergo apoptosis, for example by the expression of a gene encoding a growth suppressor or apoptosis-inducing gene product, under the control of typically, an inducible promoter. When expression of the suppressor or apoptosis-inducing product is induced, growth of the tumor cells is suppressed and/or the cells die. Growth-proficient revertant cells are identified by virtue of their continued proliferation. Alternatively, if the efficiency of gene transfer is extremely high (as has been reported for certain retroviruses) and selection for cells that have taken up DNA is employed, regulated promoters can be eliminated. In this case, the tumor suppressor or apoptosis-inducing gene could be carried on the retrovirus along with a selectable marker such as hygromycin resistance. Revertants that express the selectable marker but do not die or undergo cell cycle arrest are then isolated directly.

The invention is further directed to the identification and isolation of genes involved in cell proliferation promoting activity. This may, for example, be accomplished by selecting spontaneous revertant cell lines, analyzing their gene expression pattern, and identifying differentially expressed genes.

In other embodiments, revertants are induced with specific molecules or moieties that disrupt a particular biochemical pathway, i.e., "perturbagens". In one embodiment, the perturbagen is a DNA, encoding either a cell proliferation gene, or a protein or protein fragment acting akin to a dominant-negative mutant of cell proliferation genes, e.g., by disruption of crucial protein/protein interactions. Revertants are selected, and the cell proliferation gene or protein/protein interaction underlying the promotion of cell growth can be determined by means of identification of the nature of the perturbagen. If the perturbagen is determined to be a cell proliferation gene, the corresponding gene product can be directly analyzed. If the perturbagen acts akin to a dominant-negative mutant, e.g., by disrupting a protein/protein interaction in a signal transduction pathway, the protein acted on by the dominant-negative mutant is identified employing assays suitable for the identification of protein/protein interactions, e.g., the yeast two-hybrid system.

Analogous to DNA encoding protein fragments, peptides or peptide libraries acting as perturbagens, typically by protein/protein interaction, may be introduced in the growth suppressed cells in order to select revertants. In that case, the protein affected by the perturbing peptide is again identified employing assays suitable for the identification of protein/protein interactions.

In still alternative embodiments, revertants are induced by directing the random insertion of retroviral sequences in the genome as a means of either inactivating cellular genes (e.g., tumor suppressors) or activating proto-oncogenes. The retroviral insertion is located, and the flanking sequences, presumably including genes encoding for cell proliferation associated gene products, are characterized. Perturbagens generated as a result of such a retroviral insertion may represent aberrantly expressed normal cellular proteins or truncated versions of normal proteins. Perturbagens may also derive from RNA that interferes with the stability or translation of specific cellular mRNAs. Most typically, such RNA-based perturbagens would act in an anti-sense manner by binding to complementary mRNA sequences in the cell.

The invention is also directed to the use of the cell proliferation genes identified using the methods of the invention for the diagnosis or treatment of a disease. For example, analysis of tumor biopsies to identify the expression of a particular cell proliferation gene may serve as a valuable diagnostic indicator and may assist in guiding the therapeutic choice. Further, the identification of additional cell proliferation genes may help identify individuals who are predisposed for certain types of cancer. Predisposed individuals can be surveyed more frequently and thoroughly in order to ensure early diagnosis and treatment of the disease.

The invention is further directed to the treatment of diseases related to inappropriate or unregulated cell proliferation. For example, the invention provides methods to design, identify or develop therapeutic compounds, including antibodies, peptides, nucleic acids, etc. which will specifically interfere with the function of the identified cell proliferation gene and/or its gene product.

Finally, the invention is directed to pharmaceutical compositions comprising such therapeutic compounds, and the use of such compositions for the treatment of diseases associated with aberrant or unregulated cell proliferation.

IV. BRIEF DESCRIPTION OF THE DRAWINGS

V. DEFINITIONS

Figure 1:
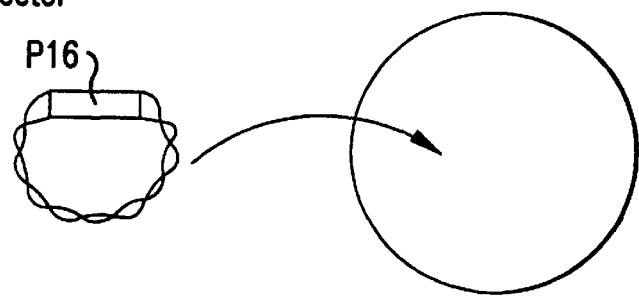
FIG. 1 depicts a flow chart of the selection systems of the present invention for the identification of cell proliferation genes.
Figure 1:
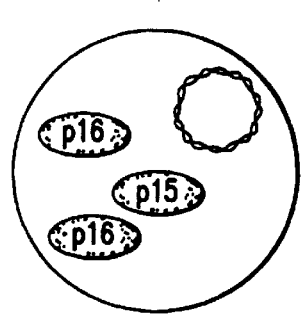
Figure 1:
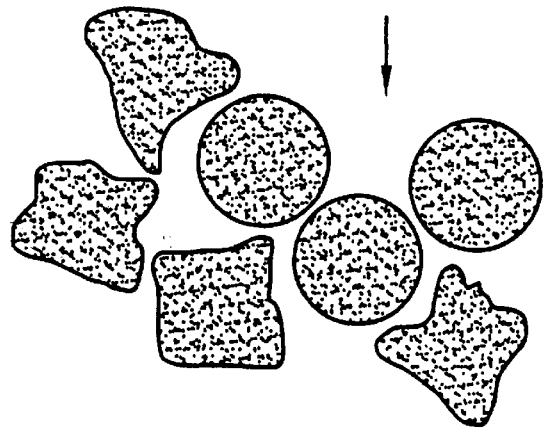

As used herein, the following term(s), whether used in the singular or plural, will have the meanings indicated:

Cell Proliferation Gene. As used herein, the term "cell proliferation gene" refers to a gene which, when aberrantly expressed or regulated, may induce or otherwise be involved in the development of cell proliferative disorders. Such cell proliferative disorders include, but are not limited to cancers, arteriosclerosis and psoriasis viral disease, as well as inflammatory conditions such as arthritis or sepsis. Cell proliferation genes include dominant transforming genes, such as oncogenes and other genes encoding products involved in the induction of cell growth and recessive cell proliferation genes, such as genes encoding tumor suppressors, genes involved in the induction of apoptosis or genes involved in viral growth.

Perturbagens. Perturbagens are molecules or moieties of defined or determinable nature, e.g., proteins, subdomains of proteins or peptides of defined sequence which, when introduced into cells or generated internally by forced expression of an endogenous gene or gene fragment, complement or disrupt a particular biochemical pathway. For example, they may act in a manner analogous to certain previously described dominant mutations. Perturbagen libraries may be generated using techniques that are similar to those employed in construction of conventional gene and cDNA libraries.

VI. DETAILED DESCRIPTION OF THE INVENTION

A. General Overview of the Invention

Utility Of Novel Cell Proliferation Genes. Apart from understanding the genetic basis for one of the major causes of cell death, discovery of new cell proliferation genes has significant medical and commercial benefits. The potential value of such genes derives from opportunities to diagnose and treat cell proliferation disorders, such as cancer, more successfully and efficiently.

First, cell proliferation genes can be of medical value in the identification of individuals predisposed to cancer. Traditional methods of cancer diagnosis have generally depended on post-symptomatic examination by localizing the tumor mass, and histological examination of tumor biopsies to classify or stage the tumor. Currently, presymptomatic detection is realized more or less routinely for a small number of cancers such as prostate carcinoma. Partin et al., 1995, *J. Urol.* 155:1336–1339; Mettlin et al., 1996, *Cancer* 77:150–159; Schroder et al., 1995, *Cancer* 76:129–134; Egawa et al., 1995, *Cancer* 76:463–472. Because early detection and surgical resection play a vital role in survival rates, methods that facilitate early diagnosis are extremely important. One way to decrease the length of time between the appearance of tumor tissue and its detection is to survey candidate patients more frequently and more thoroughly. However, such methods of surveillance are expensive; thus it is necessary to limit scrutiny to high risk individuals. Consequently, information about genetic predisposition to cancer is extremely desirable. Because most genes that influence hereditary cancer are also involved in tumor progression, isolation of genes by somatic cell genetics has the potential to uncover such predisposing genes. Germline testing for such genes offers the chance to rate an individual's probability of contracting cancer, and expensive cancer screening efforts may be limited to those most likely to benefit from them.

Second, cell proliferation genes can be of medical value in the classification of already existing tumors based on genotype. Lowe et al., 1994, *Science* 266:807–810. In the past, oncologists have relied on histological examination of biopsy specimens. Though useful, histological analyses are generally hampered by their subjectivity and imprecision. Methods that classify tumors based on their genetic composition have the potential to improve the reliability of their classification enormously. Detailed knowledge about tumor genotype may serve as a prognostic indicator for the tumor and may assist in guiding the therapeutic choice.

Finally, identification and isolation of cell proliferation genes affords important therapeutic opportunities. Numerous approaches may be pursued to use information about cell proliferation genes into therapies including, but not limited to the following: 1) transfer of wildtype tumor suppressor genes into tumor cells that have lost their activity; 2) inhibition of the activity of oncogenes in tumors, an approach that is being followed by several pharmaceutical companies in the development of ras farnesylation inhibitors; and 3) selective induction of tumor suppressor genes in normal cells to induce a state of temporary cell cycle arrest. These methods have the potential to be much more selective and efficacious than conventional chemo- or radiotherapy.

It is desirable to identify as many cell proliferation genes as possible because each one will be a candidate for medical utility.

Selection Systems For The Discovery Of Cell Proliferation Genes. The present invention is directed to selection systems for the identification of cell proliferation genes based on functional analysis. More specifically, the invention is directed to a process for selecting revertant cell lines which can be used to identify the isolation of the isolation of genes involved in such cell proliferation promoting activity, and the use of the so-identified genes for the diagnosis or treatment of a disease associated with aberrant or unregulated cell proliferation. The invention is further directed to the design and development of antibodies, peptides, nucleic acids, and other compounds which specifically interfere with the function of the identified gene and/or its gene product, and pharmaceutical compositions comprising such compounds, for the targeted treatment of diseases related to inappropriate or unregulated cell proliferation.

More particularly, the selection systems of the invention involve construction of growth arrested tumor cell lines or cells which may undergo apoptosis, for example by the expression of a gene encoding a growth suppressor or apoptosis-inducing product under the control of an inducible promoter followed by selection of revertant cells. Alternatively, revertant cells can be selected that no longer require specific growth factors. When expression of the suppressor gene is induced or specific growth factor(s) are withheld, the growth of the tumor cells is arrested. From these arrested cells, growth-proficient revertant cells can be identified by virtue of their continued proliferation. The selection systems of the invention are schematically depicted in FIG. 1.

The selection strategy provided by the present invention has several advantages. First, contrary to previously suggested methods which involved the isolation and molecular characterization of non-transformed revertants from populations of tumor cells (Fischinger et al., 1972, *Science* 176:1033–1035; Greenberger et al., 1974, *Virology* 57:336–346; Ozanne et al., 1974, *J. Virol.* 14:239–248; Vogel et al., 1974, *J. Virol.* 14:1404–1410; Cho et al., 1976, *Science* 194:951–953; Steinberg et al., 1978, *Cell* 13:19–32; Maruyama et al., 1981, *J. Virol.* 37:1028–1043; Varmus et al., 1981, *Cell* 25:23–26; Varmus et al., 1981, *Virology* 108:28–46; Mathey-Prevot et al., 1984, *J. Virol.* 50:325–334; Wilson et al., 1986, *Cell* 44:477–487; Stephenson et al., 1973, *J. Virol.* 11:218–222; Sacks et al., 1979, *Virology* 97:231–240; Inoue et al., 1983, *Virology* 125:242–245; Norton et al., 1984, *J. Virol.* 50:439–444; Ryan et al., 1985, *Mol. Cell. Biol.* 5:3477–3582; Zarbl et al., 1991, *Environmental Health Perspectives* 93:83–89), the assays disclosed herein involve positive selection; i.e., selection for growth, rather than the cessation of growth. It is easier to identify and separate growing cells from growth-arrested cells than to isolate non-transformed revertants.

Second, cultured tumor cell lines generally grow vigorously in culture. Thus, the assays of the invention can be performed in a time-efficient manner, as growing colonies can be identified, isolated, and analyzed very quickly.

Third, redundancy in growth control pathways is not a problem in the growth suppressed tumor cell lines provided and used for the selection systems of the invention, as is the case in assays based on selection for non-transformed cells. For example, in the case where a cell line is engineered to contain a gene encoding a wildtype tumor suppressor, one single restraint to growth remains. This growth restraint can be overcome by a variety of secondary changes, for example alterations in genes downstream of the particular tumor suppressor gene in the genetic pathway of growth control. Because of the fact that a single change can be sufficient to overcome the growth restraint of tumor suppressor-mediated arrest, methods that induce mutation (or perturbation) in a manner that allows recovery of the targeted gene in the cell permit isolation of additional cell proliferation genes. Accordingly, such cell proliferation genes are selected based on their inherent function as growth regulators in cells.

B. Selection Systems Based on Tumor Suppressor Genes

In one embodiment of the invention, selection systems are generated based on the growth suppression of tumor cell lines by the expression of a tumor suppressor gene, and proliferating revertants are selected.

1. Tumor Suppressor Genes

Many tumor suppressor genes cause growth arrest when overexpressed in normal cells, as well as in certain tumor cell lines. Examples for tumor suppressor genes include p53 (Lin et al., 1992, *Proc. Natl. Acad. Sci. U.S.A.* 89:9210–4), Rb (Francke et al., 1976, *Cytogenet. Cell Genet.* 16:131–134; Cavanee et al., 1983, *Nature* 305:779–784; Friend et al., 1987, *Proc. Natl. Acad. Sci. U.S.A.* 84:9059; Lee et al., 1987, *Nature* 329:642–645; Huang et al., 1988, *Science* 242:1563–1566; Harbour et al., 1988, *Science* 241:353–357; Yokota et al., 1988, *Oncogene* 3:471–475) and p16 (Kamb et al., 1994, *Science* 264:436–440; Nobori et al., 1994, *Nature* 368:753–756). Generally, tumor suppressor genes trigger growth arrest in cells at one of several positions in the cell cycle. Most frequently, however, tumor suppressors are found to cause growth arrest at the $G_1/S$ stage.

Though the details of growth control pathways are known in only a few cases, it is generally believed that overexpression of tumor suppressor genes in cell lines that contain inactivating mutations downstream in the respective growth control pathways will not have a growth inhibitory effect. In order to result in a growth arresting effect in the target cell, any particular tumor suppressor must be expressed in an appropriate cell line which contains intact downstream components of its respective growth control pathway. For example, overexpression of p16 in cells that are retinoblastoma-negative ($Rb^-$) has little or no effect on growth, while overexpression of p16 in a wide variety of $Rb^+$ lines, for example the $Rb^+$ melanoma cell line HS294T (Horuk et al., 1993, *J. Biol. Chem.* 268:541–546), causes $G_1$ arrest. Stone et al., 1996, *Cancer Res.*, in press. The reason is that Rb participates in a growth control pathway along with p16, acting downstream of p16; consequently, overexpression of p16 in the absence of Rb protein has no growth arresting effect.

In one embodiment of the invention, a selection system has been designed based on the tumor suppressor p16, which is described in more detail, infra.

In another embodiment of the invention, selection systems are designed based on the gene encoding rb. Overexpression of rb is known to cause arrest in many cell lines. As rb acts downstream of p16, revertants of rb-arrested cells are expected to contain alterations in a set of genes that overlaps with the p16-arrested revertants. Differences between these sets of genes identified by analysis of rb and p16 revertants, respectively, may, however, give interesting insight into so far unknown cellular events. Comparative experiments involving rb and p16 arrest could, for example, elucidate alternative pathways used by p16, if, for example, the growth control pathways branch upstream of rb so that p16 acts in parallel through other downstream mediators besides rb.

In still another embodiment, selection systems are generated based on the breast cancer susceptibility tumor suppressor gene BRCA1. BRCA1 has been shown to arrest growth of breast epithelial cell lines (Holt et al., 1996, *Nat. Genet.* 12:298–302), however, little is known about BRCA1's pathway of growth control. Thus, selection systems based on BRCA1 suppressed tumor cells are of compelling interest and potential utility. Analysis of revertants of BRCA1-arrested cells, e.g., in a BRCA1-overexpressing breast cancer cell line, e.g., MCF7, can be used to identify downstream mediators of BRCA1 tumor suppressor function.

In another embodiment of the invention, selection systems are designed based on the p53 pathway. Regulated expression of p53 and its downstream targets, such as the CDK inhibitor p21 induces either apoptosis or G1 arrest in a variety of cell lines. Given the prominent role of p53 in human cancer, i.e., roughly 50% of human cancers contain p53 mutations, information about other components of the p53 pathway will be extremely valuable.

In still other embodiments of the invention, other tumor suppressor genes are used in order to design selection systems for the identification of novel cell proliferation genes. In principal, any gene whose expression can be manipulated to cause cell growth arrest, can be used. Examples include, but are not limited to, WT1, VHL, BRCA2, NF1, NF2, P15, P21, P18, P19, P27, P57.

2. Reversion of Growth Arrested Phenotypes

Once arrested by expression of the tumor suppressor gene, revertant cells which continue to grow can be isolated.

In one embodiment of the invention, growth proficient random revertants are isolated. In other embodiments, reversion is induced using specific agents, i.e., perturbagens, which are introduced into the growth suppressed target cell. See, infra.

Random Revertants. Generally, growth-proficient random revertants may proliferate for one of several reasons. First, they may have gained expression of an oncogene located downstream (or possibly upstream) of the tumor suppressor in the same genetic pathway. If this is the case, tumor genes can be directly identified. Second, the revertant cells may have undergone an alteration of a signaling pathway that is parallel to the pathway within which the ectopically expressed tumor suppressor gene acts. Alternatively, the revertant cells may have lost expression of the tumor suppressor gene used to arrest them in the first place. Finally, the cells may have lost expression of tumor suppressor genes that act downstream of the ectopically expressed tumor suppressor gene.

In a specific embodiment of the invention, p16 is ectopically expressed in an $Rb^+$ cell line, such as the melanoma HS294T line, under the control of an IPTG inducible promoter. As a consequence of the p16 expression, the cells arrest in the $G_1$ phase of the cell cycle, resulting ultimately in death of the vast majority of these cells. The revertant cells are identified and isolated, for example, by placing the arrested cells in 96-well plate wells. After about three (3) weeks, revertant clones are transferred into new culture dishes, expanded and characterized.

In a specific working example described herein, infra, six revertant cell lines derived from the HS294T/p16 cell line, which expressed p16 when induced with IPTG, were isolated. Interestingly, the revertant cell lines typically exhibited growth properties that are similar to their parental line. For example, determination of the proportion of cells in $G_1$ under conditions of asynchronous growth by flow cytometry revealed that four of the six lines had a proportion of cells in $G_1$ similar to the parental HS294T line used to engineer the arrestable line, i.e., roughly 3–4 times as many $G_1$ cells as $G_2$ cells. One line appeared to have a more equal proportion of $G_1$ and $G_2$ cells. The sixth line turned out to have some residual sensitivity to p16, since the percentage of $G_1$ cells varied depending on whether expression of p16 was induced by addition of IPTG to the medium. Unlike the other five lines, this line had more cells in the $G_1$ phase when p16 was expressed than in its absence, suggesting that the line had not become fully insensitive to p16 expression, but only partially insensitive.

When the six lines were characterized for the presence of various proteins thought to be involved in the p16 growth control pathway, interesting results were obtained. Four of the six lines had lost expression of p16. Presumably these lines escaped from induced p16 arrest by eliminating the tumor suppressor gene, or alternatively, by preventing its expression. The fifth cell line had lost expression of Rb. This is consistent with the notion that Rb acts downstream of p16 in a common pathway for growth control. Finally, the sixth cell line appeared to contain the expected levels of p16 and Rb genes. The levels of the potential oncogenes CDK4 and cyclin D1, also thought to act in the p16 growth control pathway, appeared normal as well. Thus, the sixth revertant cell line contained alterations in the expression or function of a gene of unknown identity. Based on its function, this gene is involved in the induction of the uncontrolled cell proliferation and thus possibly in the development of cancer. This cell line permits the identification of a novel cell proliferation gene.

Induced Revertants. In another embodiment of the invention, the identification of cell proliferation genes does not rely on the selection of random revertants. Growth-proficient revertants are induced using specific types of "mutagenic" agents, referred to as "perturbagens". Revertant cells are selected, and the gene or genes that allow escape from arrest are identified.

In one embodiment, the perturbagen is DNA encoding a cell proliferation gene, or, alternatively, dominantly active protein subdomains or peptide sequences, used to disrupt the action of endogenous tumor suppressors or oncogenes, e.g., by interfering with crucial protein/protein interactions. Revertants are selected, and the cell proliferation gene or protein/protein interaction underlying the promotion of cell growth is determined by means of identification of the nature of the perturbagen.

If the perturbagen is determined to be a cell proliferation gene, it can be directly analyzed. For example, the perturbagen sequence is recovered using the Polymerase Chain Reaction (PCR) and sequenced using standard methods. If the perturbagen sequence is identical or similar to sequences in a public database such as GenBank or dbEST, then it can be directly identified. Alternatively, if a portion of the sequence is known, or even in the absence of any identification, the entire sequence of the perturbagen can be identified by isolating cDNA clones and standard recombinant DNA methodology.

The target of the perturbagen can be identified using a variety of methods. For example, if the perturbagen is acting akin to a dominant-negative mutant, e.g., by disrupting a protein/protein interaction in a signal transduction pathway, the protein affected by the dominant-negative mutant is identified using assays suitable for the identification of protein/protein interactions, e.g., the yeast two-hybrid system. Perturbagens can also act at the RNA level, in which case yeast two-hybrid analysis would be insufficient to identify the perturbagen target. In most cases such perturbagens are expected to act through an anti-sense mechanism and the targets would are identified based on the complement of the perturbagen sequence.

For introduction of the perturbagens, if genes encoding for entire proteins or protein fragments are employed as perturbagens, perturbagen libraries are constructed from mRNA of any cell line or tissue and inserted into expression vectors such as retroviruses which serve as highly efficient delivery systems. Such libraries, when introduced into cells, may act as mutagens. If the cells are placed under stringent selection for a particular trait such as growth, perturbagen-induced variants can be isolated. Wildtype cells die, but cells that receive specific perturbagen sequences that interfere with growth regulation pathways grow. Contrary to somatic mutations of growth suppressor genes, which are recessive, perturbagens that impair the activity of a gene product by, e.g., interfering with protein/protein interactions, are dominant, affecting the products of both alleles of a genetic locus. Alternatively, perturbagens are introduced into cells and monitored in a transient fashion. Transient gene expression is efficient and readily achieved. Electroporation and various other methods of gene delivery are suitable for transient expression monitoring of the introduced perturbagens. In cases where dominant negatively acting perturbagens are employed, libraries may be constructed from randomly primed mRNA and inserted into expression vectors, such as retroviruses. Alternatively, the libraries are fused to degradation promoting domains.

In alternative embodiments, DNA libraries that encode random peptide are employed. Alternatively, combinatorial chemical libraries, most typically peptide libraries, may be employed as perturbagens.

In still alternative embodiments, revertants are induced by directing the random insertion of retroviral sequences in the genome as a means of either inactivating cellular genes (e.g., tumor suppressors) or activating proto-oncogenes. The retroviral insertion is located, and the flanking sequences, presumably including genes encoding for cell proliferation associated gene products, are characterized. Perturbagens generated as a result of such a retroviral insertion may represent aberrantly expressed normal cellular proteins or truncated versions of normal proteins. Perturbagens may also derive from RNA that interferes with the stability or translation of specific cellular mRNAs. Most typically, such RNA-based perturbagens would act in an anti-sense manner by binding to complementary mRNA sequences in the cell.

Recovery and identification of the perturbagen sequences and their targets is accomplished with standard procedures, including the polymerase chain reaction (PCR) and the yeast two hybrid system. See, Section VI.E., infra.

Figure 2A:
FIGS. 2A and 2B depict a flow chart exemplifying the use of perturbagens as a tool for the induction of revertants in the selection systems of the present invention for the identification of cell proliferation genes and protein/protein interactions.
Figure 2A:
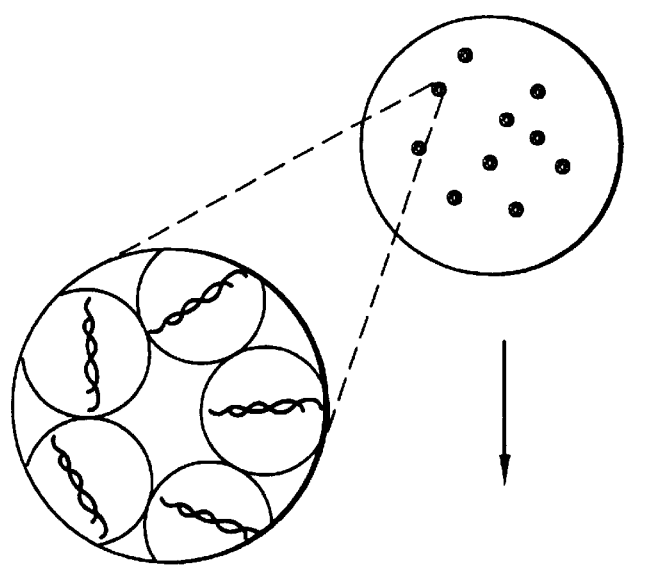
Figure 2A:
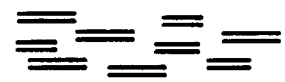
Figure 2B:
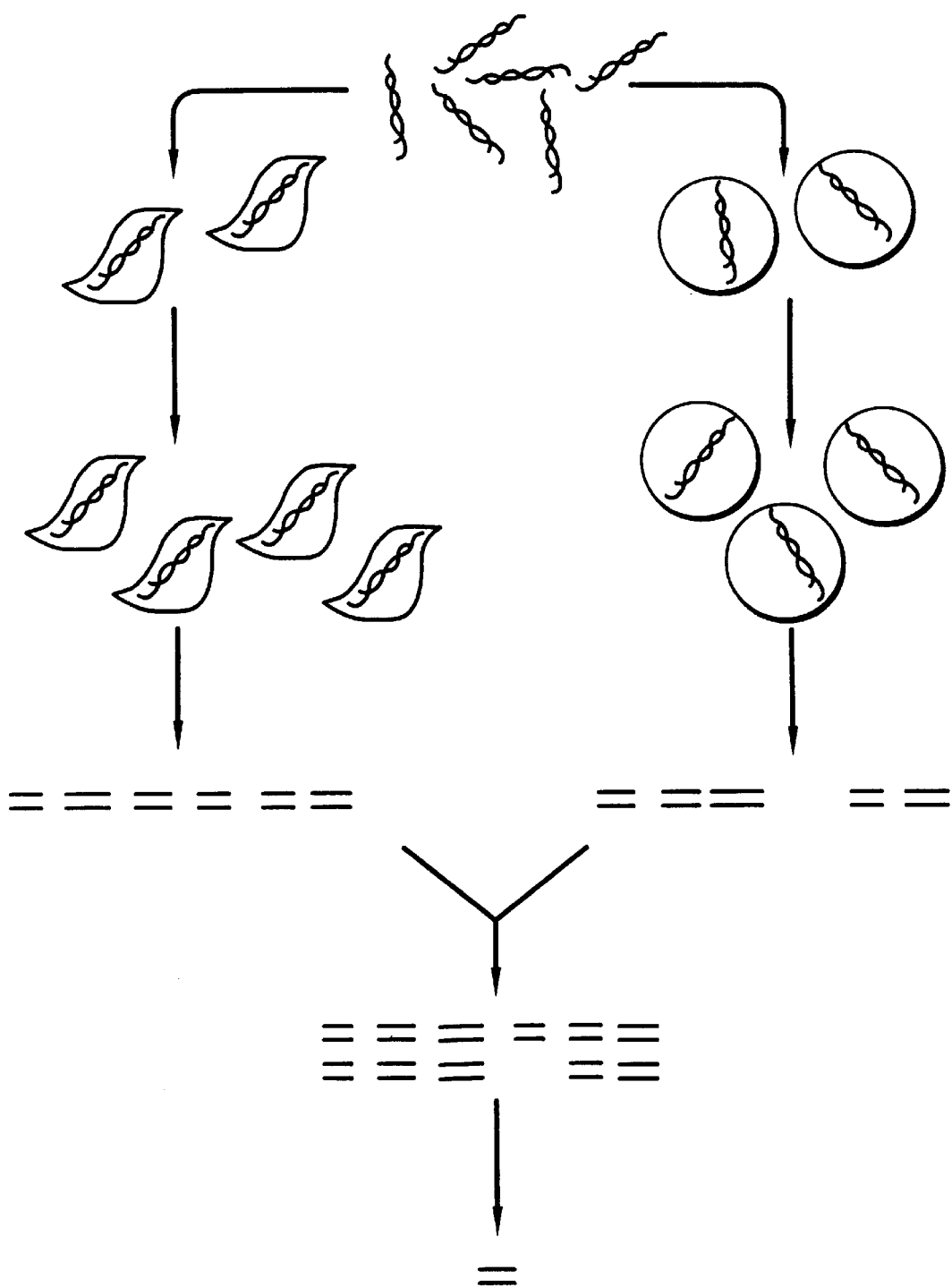

The use of perturbagens for the induction of revertants in the selection systems of the present invention is depicted schematically in FIGS. 2A and 2B.

Once isolated, the perturbagen can be reintroduced into the same cell it was isolated from, or into different cell types to further characterize the properties of the molecule.

C. Other Selection Systems

CDK Inhibitors. In one embodiment of the invention, selection systems are generated based on expression of CDK inhibitors in suitable host cells.

All CDK inhibitors defined to date, including p15, p16, p18, p19, p21, p27, p57 cause cell cycle arrest when they are overexpressed in certain cell lines. In some cases, such as p16, some details are already known with respect to downstream pathway components. In other cases, most details of the pathway of growth control within which the genes function are still to be elucidated. Apart from their preferred in vitro targets, i.e., CDK4 and CDK6 in the cases of p15, p16, and p18, and CDK4, CDK6, and CDK2 (and CDK4, CDK6) in the case of p21, p27, and p57, the identification of components of the pathways that act downstream by reversion selection systems will greatly facilitate the ability to manipulate these growth control pathways to achieve a therapeutic advantage.

Many cell lines respond to ectopic expression of CDK inhibitors by entering a state of arrest, and may be used for CDK inhibitor based selection systems accordingly. Exceptions are lines that have lost the activity of downstream mediators of the CDK inhibitor pathways. For example, Rb−cell lines cannot be forced into arrest by overexpression of p16. In addition, certain cell lines may have incurred mutations in downstream genes other than Rb. For instance, specific mutations in CDK4 render the mutant protein resistant to inhibition by p16. This defect has been shown to result from single amino acid substitutions in CDK4 protein that prevent binding of p16 to the enzyme without impairing catalytic activity. Wolfel et al., 1995, Science 269:1281–1284. Similar mutations could interfere with the ability of other CDK inhibitors to carry out their tumor suppressor activity. Thus, it is critical to select cell lines that have intact growth control pathways downstream of the particular CDK inhibitor such that they respond to ectopic CDK inhibitor expression by entering cell cycle arrest.

Oncogene Pathways. In another embodiment, selection systems are generated based on dissection of oncogene pathways. For example, a dominant-negative oncogene or a dominant-negative fragment of an oncogene of interest may be ectopically expressed such that growth is inhibited or apoptosis is induced. Selection and analysis of revertants results in the identification of genes encoding products which play a role downstream in the oncogene's pathway.

Many forms of dominant-negative oncogene mutants have been engineered. For example, in the case of receptor tyrosine kinases, receptor mutants lacking an intact enzymatic domain have been shown to dominant-negatively inhibit the function, and thus signal transduction, of the wild-type receptor. Redemann et al., 1992, Mol. Cell. Biol. 12:491–498; Kashles et al., 1991, Mol. Cell. Biol. 11:1454–1463; Millauer et al., 1994, Nature 367: 576–579. Further, naturally occurring dominant negative oncogenes have been identified, which have variable effects that depend heavily on the specific cell line in which they are expressed. Below (TABLE I) are listed several examples from the literature of the effects of dominant negative proto-oncogenes on the growth and/or transformation properties of specific cells.

TABLE I

| GENE | RECIPIENT CELL | EFFECT | REFERENCE |
| --- | --- | --- | --- |
| c-JUN | MCF7 | inhibition of colony formation | Chen et al., 1996, Mol. Carcinog. 15: 215–226 |
| EGF-R | Rat-1 | inhibition of DNA synthesis | Daub et al., 1996, Nature 379: 557–560 |

TABLE I-continued

| GENE | RECIPIENT CELL | EFFECT | REFERENCE |
| --- | --- | --- | --- |
| GRB2 | NIH3T3 | inhibition of transformation | Xie et al., 1995, J. Biol. Chem. 270: 30717–30724 |
| RAF | NIH3T3 | inhibition of growth in soft agar | Denko et al., 1995, Somat. Cell. Mol. Genet. 21: 241–253 |
| RAF | GH4 | ras-induced promotor activation | Pickett et al., 1995, Mol. Cell. Biol. 15: 6777–6784 |
| MAX | NIH3T3 | natural growth regulation | Arsura et al., 1995, Mol. Cell. Biol. 15: 6702–6709 |
| RAS | SK-N-MC | inhibition of ERK2 activation | van Weering et al., 1995, Oncogene 11: 2207–2214 |
| SRC | endothelial | inhibition of c-FOS activation | Simonson et al., 1996, J. Biol. Chem. 271: 77–82 |

In principle, dominant negative proto-oncogenes can serve in the same way as tumor suppressor genes to arrest cells or prevent cell growth under certain conditions, thus providing a basis for selection of revertants.

Tumor Formation And Metastasis In Vivo. In another embodiment, selection systems are generated based on the observation that some tumor cell lines do not form tumors when injected into immunocompromised mice, while others do. For example, premalignant melanoma cell lines typically are nontumorigenic when placed in immunocompromised mice. In one embodiment, such premalignant melanoma cells are injected subcutaneously in nude mice, and tumors are selected following injection of such premalignant cells. These tumors arise from variants of the premalignant parental cells that have acquired mutations that permit growth in the mouse, ultimately forming identifiable tumors. Thus, such a mouse tumor formation system provides a mechanism for selecting cell revertants that have activated proto-oncogenes or inactivated tumor suppressor genes that are involved directly in the transformation from a nontumorigenic phenotype to a tumorigenic one. These revertants can subsequently be studied to identify the proto-oncogenes or tumor suppressor genes involved in tumor formation.

In addition, overexpression of particular genes in tumor cell lines can render a tumorigenic line non-tumorigenic. Again, if such cells are injected in immunocompromised animals, for example subcutaneously, revertant cells may be selected that contain alterations in important cell proliferation genes. Genes that contribute to tumor formation in vivo may be directly analyzed and recovered.

Apoptosis. In another embodiment, selection systems are generated based on the phenomenon of apoptosis, i.e., the ability of cells to undergo programmed cell death.

Apoptosis, is a mechanism important for the proper development of tissues. It is also implemented by the body during lymphocyte maturation in order to remove self-reactive lymphocytes. Finally, it serves as an important mechanism for maintaining the integrity of fully developed tissues in the context of various types of damage. For instance, skin cells exposed to significant levels of ultraviolet light undergo apoptosis, presumably to eliminate cells that have a high likelihood of being damaged in a way that is harmful to the long term health of the organism. Such "sunburned" cells, if they were not removed, might give rise to cancerous growth at an increased frequency. Ziegler et al., 1994, Nature 372:773–776.

In fact, apoptosis appears to be a general mechanism used in many tissues for eliminating premalignant, partially transformed cells. When these mechanisms are inactivated by mutation of genes such as p53, cancer cells are at a selective advantage compared to normal cells and compared to tumor cells in which apoptotic pathways are still intact. Such apoptosis-deficient cells are able to grow (or avoid self-inflicted death) where others are not. Ziegler et al., 1994, *Nature* 372:773–776.

Cells in culture can be induced to undergo apoptotic death by a variety of stimuli, depending on the particular cells. For example, certain cells enter apoptosis after exposure to glucocorticoids, tumor necrosis factors, or other natural agents. In addition, many cell types undergo apoptosis when exposed to radiation or chemotherapeutics. Further, cells may be engineered to contain genes which have been implicated in the control of or participation in apoptosis under the control of an inducible promoter. Such genes include, but are not limited to bcl-2 (Korsymeyer, 1992, *Immunol. Today* 13:285–288), c-myc (Shi et al., 1992, *Science* 257:212–214; Evan et al., 1992, *Cell* 69:119–128), p53 (Rotter et al., 1993, *Trends Cell. Biol.* 3:46–49), TRPM-2/SGP (Kryprianou et al., 1991, *Cancer Res.* 51:162–166), and Fas/APO-1 (Itoh et al., 1991, *Cell* 66:233–243). Cell types which can be induced to undergo apoptosis include, for example, lymphocytes and tumor cells derived from lymphocytes. Activation of the FAS antigen receptor in maturing lymphocytes activates an apoptosis program. If the FAS antigen is activated either by exogenous application of a FAS antibody (Velcich et al., 1995, *Cell Growth Differ.* 6:749–757) or by ectopic expression of an activated form of the receptor, revertants that survive can be selected. Some of these revertants contain mutations in genes downstream of the FAS antigen that operate in the same apoptotic pathway as FAS. Treatment with certain steroid hormones or cross-linking of the T cell receptors on the cell surface using, for example, an antibody, can also induce apoptosis in lymphocytes and related cell or tumor lines. The 3DO line, for instance, responds to receptor cross-linking by undergoing apoptosis (Vito et al., 1996, *Science* 271:521–525), while murine thymoma W7 cells undergo apoptosis in response to dexamethasone (Bourgeois et al., 1993, *Mol. Endocrinol.* 7:840–851). Other cell lines undergo apoptosis when cultured at low density or in the absence of specific serum factors (Ishizaki et al., 1995, *Mol. Endocrinol.* 7:840–851). In Friend erythroleukemia cells, overexpression of p53 results in apoptosis (Abrahamson et al., 1995, *Mol. Cell. Biol.* 15:6953– 6960). Overexpression of certain oncogenes in some tumor lines can, paradoxically, also induce apoptosis (Harrington et al., 1994, *Curr. Opin. Genet. Dev.* 4:120–129). The morphogen retinoic acid induces programmed cell death in the P19 embryonic stem cell (Okazawa et al., 1996, *J. Cell Biol.* 132:955–968). It is also possible to use various forms of trauma to induce apoptosis in a variety of cell types. For instances, treatment of many cell types by DNA-damaging agents (e.g., certain chemotherapeutics, radiation) causes an apoptotic response. Each of these methods provides the basis for selecting revertants that fail to undergo apoptosis. These revertants can be used in turn to recover genes involved in pathways of apoptosis.

Accordingly, the ability of cells to initiate apoptosis is used for the development of a genetic selection system; revertants that fail to die are isolated.

Contact Inhibition. In still another embodiment, selection systems are generated based on the fact that loss of growth regulation of cells is frequently reflected in the loss of contact inhibition of cell proliferation. Accordingly, pools of cells which have lost contact inhibition are used to isolate contact-inhibited revertants.

Most normal cells and many cell lines do not grow indefinitely in the body or in culture, rather they are inhibited by contact with their neighbors; this state of arrest is known as contact inhibition. For example, melanoma cell lines can be cultured under conditions where they become inhibited by contact (Valyi-Nagy et al., 1993, *Int. J. Cancer* 54:159–165), as can neural precursor lines transformed by polyoma large tumor (T) gene (Galiana et al., 1995, *Proc. Natl. Acad. Sci. U.S.A.* 92:1560–1564), derivatives of colon HT29 cells (Velcich et al., 1995, Velcich et al., 1995, *Cell Growth Differ.* 6:749–757), human umbilical vein endothelial cells (Gaits et al., 1995, *Biochem. J.* 311:97–103), nonparenchymal epithelial cells (Johnson et al., 1995, *Cancer Lett.* 96:37–48), and many others.

In the past, the phenomenon of contact inhibition of cells has been used to select variants that continue to grow when saturation of the culture dish bottom has been reached. Foci have been isolated, comprised of cells that no longer respond to contact inhibitory signals and are often more likely to form tumors in animals than their parental counterparts. The initial identification of cellular oncogenes involved such an experimental approach. Land et al., 1983, *Nature* 304:596–602; Copeland et al., 1979, *Cell* 17:993–1002.

Growth Factors. In still another embodiment, selection systems are generated based on the growth factor requirement of mammalian cells.

Many mammalian cells in culture require the presence of factors in the media which permit growth. In the absence of such factors, many cell types do not grow in tissue culture. In several cases the relevant factors have been defined. For example, in the absence of exogenous interleukin-2, certain T cells do not proliferate in culture. Melanoma formation proceeds via a series of steps through which normal melanocytes evolve into fully metastatic melanomas. During this process the progressing tumor cells gradually lose their requirements for specific exogenous factors (TABLE II). Normal melanocytes require factors such as phorbol ester, fibroblast growth factor (FGF), melanocyte stimulating hormone-alpha (MSH-α), insulin, or insulin-like growth factor-1 (IGF-1). In contrast, metastatic melanoma cells often require none of these factors. Cell lines with intermediate phenotypes require progressively fewer factors. This transition can be studied in culture such that factor-independent variants are isolated from earlier stage lines. These variants contain mutations that allow the cell to bypass the requirement for one of the factors. Thus, they can be used as the starting point for identification of genes that participate in the pathway of tumorigenesis involving escape from growth factor requirements.

TABLE II

GRADUAL LOSS OF THE GROWTH FACTOR REQUIREMENT OF MELANOCYTES DURING MELANOMA FORMATION.

MELANOMA PROGRESSION

| Cell Type | Requirements | Phenotype |
|---|---|---|
| Melanocyte | TPA | Normal |
|  | FGF |  |
|  | α-MSH |  |
|  | IGF-1 |  |
| Nevus | TPA | Similar to melanocyte |
|  | FGF |  |
|  | α-MSH |  |
|  | IGF-1 |  |

TABLE II-continued

GRADUAL LOSS OF THE GROWTH FACTOR REQUIREMENT OF MELANOCYTES DURING MELANOMA FORMATION.

MELANOMA PROGRESSION

| Cell Type | Requirements | Phenotype |
|---|---|---|
| Early melanoma | FGF1 | Immortalized |
| | α-MSH | |
| | IGF-1 | |
| Primary melanoma | IGF-1 | Tumorigenic |
| Metastatic melanoma | | Migratory |

Accordingly, the growth factor requirement of cells can be exploited to provide a powerful selection system. More specifically, a particular growth factor is removed from the media, resulting in death of the vast majority of cells. Subsequently, variants that continue to grow in the absence of the factor are selected; the mutations that have eliminated the function of the regulatory pathway that prevents growth in the absence of the factor are identified and the corresponding genes recovered.

Growth In Isolation. In still another embodiment, selection systems are generated based on the observation that many cells in culture do not grow in isolation or at low density in culture. They require neighboring cells, presumably because these cells produce and secrete into the media growth factors that are necessary for growth. If these factors do not reach a certain threshold concentration, the cells cannot grow.

Many cell lines can be grown in isolation from other neighbors only with great difficulty. For example, many T cell lines can only be cloned when the individual cells are placed on a "feeder layer" of other cells, i.e., cells that have been treated such that they do not divide, but continue to produce growth factors that allow the T cell to proliferate into clone of descendants. This process of clonal growth can be used to select variants that are able to grow in the absence of a feeder layer.

Accordingly, revertant cells are selected that do grow at low density in colonies. These cells presumably contain alterations in genes involved in a pathway of growth dependence on neighbors, and hence, on secreted factors.

Immortalization. In still another embodiment, selection systems are generated based on the observation that normal cells, e.g., primary mammalian cells, have a finite life span in culture; they undergo a certain number of cell doublings and then die. The length of their life in culture depends on a variety of factors including the tissue of origin, the age of the animal from which the cells were derived, and the nature of the growth media. The period during which massive cell death occurs as the cells reach their age limit is known as the crisis phase.

Accordingly, variants are selected that survive the crisis phase; these cells have undergone changes that lead to immortalization. In principle, this serves as a selection for immortalized cells with mutations in genes that normally limit life span.

D. Generation Of Growth Arrested Tumor Cell Lines As Selection Systems

Where the generation of the selection systems of the invention involves the expression of a growth suppressing or apoptotic gene in cultured cells, the nucleotide sequence encoding for the apoptosis regulator or inducer, or the growth suppressor, e.g., a tumor suppressor gene or a dominant-negative oncogene or oncogene mutant, or a functional equivalent thereof, is inserted into an appropriate expression vector, i.e., a vector which contains the necessary elements for the transcription and translation of the inserted coding sequence, and is introduced into the host cell system.

Expression Systems For The Expression Of The Growth Suppressing Genes. Typically, where a gene encoding the growth suppressor or the apoptosis-inducing product is introduced in a transformed cell, an inducible promoter system is used for the control of its expression. An inducible promotor permits growth of the cells that contain the expression construct under conditions where the promotor is turned off. When desired, the promotor can be induced and the cells become growth arrested due to the expression of the tumor suppressor gene. Alternatively, if the efficiency of gene transfer is extremely high (as has been reported for certain retroviruses) and a selection for cells that have taken up DNA is employed, regulated promoters may be dispensed with. In this case, the tumor suppressor gene or apoptosis-inducing gene is carried on the retrovirus along with a selectable marker such as hygromycin resistance. Revertants that express the selectable marker but do not die or undergo cell cycle arrest are then isolated directly.

Several suitable inducible promoters are established for use in mammalian cells, and many more can be envisioned. Examples include, but are not limited to, interferon inducible promoter systems, such as the promoter for 3'-5' poly (A) synthetase or the Mx protein, which are induced by, e.g., a poly inosine and cytosine duplex Schumacher et al., 1994, Virology 203:144–148. Other examples include the HLV-LTR, which can be induced with, e.g., dimethylsulfoxide (DMSO), or the metallothionein promoter system, which is inducible by heavy metal ions Haslinger et al., 1985, Proc. Natl. Acad. Sci. U.S.A. 82:8572–8576. Other inducible promoters include the tetracycline and lac repressor systems, where a repressor, i.e., tetracycline or IPTG, respectively, maintains the promotor in an inactive state. Thus in the absence of exogenous tetracycline or IPTG the promoter is suppressed (tet system: Gossau and Bujard, 1992, Proc. Natl. Acad. Sci. U.S.A. 89:5547–5551; lac system: Fieck et al., 1992, Nucleic Acid Res. 20:1785–1791).

In a specific embodiment of the invention, a IPTG lac switch system has been used as inducible promoter system. Specifically, the promotor of the inducible construct contained sequences from the Rous Sarcoma Virus (RSV) long terminal repeat (LTR) that act as a potent transcriptional initiator located upstream of the coding sequence of the gene to be expressed (in the specific example disclosed herein, p16). Between the translational start site and the RSV LTR were operator sequences derived from the E. coli lac operon. These sequences are sufficient for binding of the lac repressor. In the presence of functional lac repressor, transcription from the RSV LTR is dramatically reduced by the lac operator sequences. However, when IPTG is added to the culture media, lac repressor molecules are prevented from blocking the transcription of the gene to be expressed; the desired mRNA is synthesized and protein is produced.

Further, proper expression of genes encoding the growth suppressor or the apoptosis-inducing product may require specific initiation signals for efficient translation of inserted cell proliferation gene encoding sequences. These signals include the ATG initiation codon and adjacent sequences. In cases where the entire gene, including its own initiation codon and adjacent sequences, is inserted into the appropriate expression vector, no additional translational control signals may be needed. However, in cases where only a portion of the gene encoding the growth suppressor or the apoptosis-inducing product is inserted, exogenous translational control signals, including the ATG initiation codon, must be provided. Furthermore, the initiation codon must be in phase with the reading frame of the cell proliferation gene encoding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See, Bittner et al., 1987, *Methods in Enzymol.* 153:516–544.

Though transient expression of the growth suppressor or the apoptosis-inducing product might be sufficient in some cases, most typically the gene encoding the growth suppressor or the apoptosis-inducing product will be stably expressed in the host cells. Host cells are transformed with DNA encoding the desired product controlled by appropriate expression control elements, including a promoter, which typically is inducible, see, supra, enhancer sequences, transcription terminators, polyadenylation sites, etc., and a selectable marker.

Following the introduction of foreign DNA, engineered cells are allowed to grow for 1–2 days in an enriched media, and then switched to a selective media. The selectable marker in the recombinant plasmid confers resistance to the selection and allows cells to stably integrate the plasmid into their chromosomes and grow to form colonies. The colonies are cloned and expanded into cell lines.

A variety of transfection techniques are currently available to transfer DNA in vitro into cells; including calcium phosphate-DNA precipitation, DEAE-Dextran transfection, electroporation, liposome mediated DNA transfer or transduction with recombinant viral or retroviral vectors, and may be used in the methods of the present invention.

A number of selection systems may be used in the invention, including but not limited to the herpes simplex virus thymidine kinase (Wigler et al., 1977, *Cell* 11:223), hypoxanthine-guanine phosphoribosyltransferase (Szybalska and Szybalski, 1962, *Proc. Natl. Acad. Sci. U.S.A.* 48:2026), and adenine phosphoribosyltransferase (Lowy et al., 1980, *Cell* 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, *Proc. Natl. Acad. Sci. U.S.A.* 77:3567; O'Hare et al., 1981, *Proc. Natl. Acad. Sci. U.S.A.* 78:1527); gpt, which confers resistance to mycophenolic acid (Mulligan and Berg, 1981, *Proc. Natl. Acad. Sci. U.S.A.* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes. Additional selectable genes have been described, namely trpB, which allows cells to utilize indole in place of tryptophan; hisD, which allows cells to utilize histinol in place of histidine (Hartman and Mulligan, 1988, *Proc. Natl. Acad. Sci. U.S.A.* 85:8047); and ODC (ornithine decarboxylase) which confers resistance to the ornithine decarboxylase inhibitor, 2-(difluoromethyl)-DL-ornithine, DFMO (McConlogue, 1987, in: *Current Communications in Molecular Biology*, Cold Spring Harbor Laboratory ed.).

In the case where high-efficiency retroviral delivery systems are used for the generation of cell lines, selection systems are not necessarily required due to the high efficiency of retroviral gene transfer. Retroviral expression systems which are engineered to encode and express the desired recombinant gene may involve the use of infectious or non-infectious particles that undergo only a single initial round of infection. In the former case, the genome of the virus maintains regulatory sequences, structural genes, and packaging signals necessary for the generation of new virus particles, while genes conferring oncogenic potential are removed. After the retroviral proteins are synthesized, the host cell packages the RNA in new particles, which can undergo further rounds of infection.

Preferably, however, non-infectious retroviral vectors are used in the present methods, which require a helper virus to provide the structural genes necessary to encode viral structural proteins. The helper virus' packaging signal which is required to encapsulate the helper viral RNA into particles is destroyed, and as a result only the recombinant retroviral vector containing a functional packaging signal and the gene of interest, but lacking the retrovirus' structural components can be incorporated in an particle. Consequently, the resulting retrovirus can infect a target cell, and its genetic information may be inserted into the host's genome; however, the so transferred genetic information is biologically contained because genes essential for viral growth are not provided. Methods for constructing and using retroviral expression systems are well known in the art and reviewed, for example, in Miller and Rosman, 1992, *Biotechniques* 7:980–990.

Identification Of Transfectants Or Transformants That Express The Growth Suppressing Or Apoptotic Gene. The host cells which contain the coding sequence and which express the biologically active gene product may be identified by at least four general approaches; (1) DNA-DNA or DNA-RNA hybridization; (2) the presence or absence of "marker" gene functions; (3) assessing the level of transcription as measured by the expression of cell proliferation gene mRNA transcripts in the host cell; and (4) detection of the gene product as measured by immunoassay or by its biological activity.

In the first approach, the presence of the sequence encoding the desired product inserted in the expression vector is detected by DNA-DNA or DNA-RNA hybridization using probes comprising nucleotide sequences that are homologous to the sequence encoding the desired product, respectively, or portions or derivatives thereof.

In the second approach, the recombinant expression vector/host system is identified and selected based upon the presence or absence of certain "marker" gene functions (e.g., thymidine kinase activity, resistance to antibiotics, resistance to methotrexate, transformation phenotype. For example, if the gene encoding the growth suppressor or the apoptosis-inducing product is inserted within a marker gene sequence of the vector, recombinants containing the gene encoding the growth suppressor or the apoptosis-inducing product are identified by the absence of the marker gene function. Alternatively, a marker gene is placed in tandem with gene encoding the growth suppressor or the apoptosis-inducing product under the control of the same or different promoter used to control the expression of the sequence encoding the growth suppressor or the apoptosis-inducing product. Expression of the marker in response to induction or selection indicates expression of the sequence encoding the growth suppressor or the apoptosis-inducing product.

In the third approach, transcriptional activity for the gene encoding the growth suppressor or the apoptosis-inducing product is assessed by hybridization assays. For example, RNA is isolated and analyzed by Northern blot using a probe homologous to the gene encoding the desired product or particular portions thereof. Alternatively, total nucleic acids of the host cell are extracted and assayed for hybridization to such probes.

In the fourth approach, the expression of the gene protein product is assessed immunologically, for example by Western blots, immunoassays such as radioimmunoprecipitation, enzyme-linked immunoassays and the like. The ultimate test of the success of the expression system, however, involves the detection of the biologically active gene product. A number of assays can be used to detect activity of the gene encoding the growth suppressor or the apoptosis-inducing product including, but not limited to, transformation assays, growth assays, etc.

E. Identification and Isolation of Novel Cell Proliferation Genes

The identified revertant cells obtained as described above are used in the methods of the invention to reveal and characterize novel cell proliferation genes.

In one embodiment, subtractive hybridization of cDNA is used to identify sequences that are responsible for the reverted phenotype. In this process, cDNA probes are prepared from the parental cell line and one of the selected revertants. These probes are then hybridized to filters generated from cDNA libraries or genomic DNA libraries. Most preferably, the source of the libraries may be the parental cell line, the revertant line or both. The filters are probed with the two probes separately, most conveniently in duplicate, and differences in signal intensity are noted. Clones of interest containing sequences that show different signal strengths in the hybridizations to the parental probe and the revertant probe are identified and isolated. A general protocol for subtractive hybridization of cDNA can be found, among other places, in Sambrook et al., 1994, *Molecular Cloning: A Laboratory Manual*, Cold Spring Harbor Press, New York.

In another embodiment, a probe is generated that is enriched for differentially expressed sequences. More specifically, cDNA is synthesized from the parental or revertant cell lines and hybridized in solution against mRNA from the other line. Shared sequences are removed from the cDNA probe by, for example, avidin-biotin capture, by binding to hydroxyapatite, or by any other suitable procedure. The remaining single stranded and thus unique cDNA sequences are then used to probe cDNA library filters to identify and isolate the differentially expressed sequences; alternatively, they may be cloned and examined directly. Hedrick et al., 1984, *Nature* 308:149–153.

In still another embodiment, differentially expressed genes are detected by cloning and sequencing of high numbers of cDNA sequence fragments from the parent and revertant sources. Comparison of the sequences then leads to information about relative expression levels. This, for example, can be accomplished by sequence analysis of 3' expressed sequence tags (ESTs), a method pioneered by The Institute for Human Genome Research (TIGR) and by Human Genome Sciences, Inc. (HGS). Lennon et al., 1996, *Genomics* 33:151–152. An alternative is to analyze small sequence tags cloned in multiple copies into plasmids or phage, a method known as Serial Analysis of Gene Expression (SAGE). Velculescu et al., 1995, *Science* 270:484–487.

In still another embodiment polymerase chain reaction (PCR) is employed for identification of differentially expressed sequences, in an approach known as "differential display." The method takes advantage of the pseudo-random amplification that ensues when multiple primers of arbitrary sequences are placed in a reaction tube with random-primed cDNA. Certain fragments amplify and these are analyzed by denaturing gel electrophoresis. If two different cDNA samples are used separately, i.e., one from a parental line, one from a revertant, the two PCR-amplified product sets can be run side-by-side on a gel. The intensities of different sized bands are compared, bands of different intensity are excised from the gel, reamplified and cloned for further analysis. Zhao et al., 1995, *Biotechniques* 18:842–850.

In still other embodiments, gene expression is monitored and compared using protein levels as the output parameter. One method of differential protein analysis, for example, involves comparison of two-dimensional protein gels, whereby one dimension is non-denaturing, the second dimension is denaturing, to identify protein spots that are non-identically expressed in the two samples. Differences in samples of total protein isolates from the parental line are identified, the corresponding proteins are then purified and sequenced, in order to ultimately gain enough information for cloning of the corresponding gene or cDNA.

In still another embodiment, an array of oligonucleotides or cDNA fragments gridded out on a solid support is used as the probe against labeled cDNA prepared from the revertant cell line. The hybridization signals of the cDNAs are used to determine which sequences are expressed at different levels. Schena et al., 1995, *Science* 270:467–470.

Isolation Of The Cell Proliferation Gene Or Its cDNA. Once a DNA or peptide fragment of the cell proliferation gene has been identified and sequenced, the corresponding gene or cDNA clone is isolated by standard methods described in, for example, Sambrook et al., supra.

Gene Recovery In Revertants Induced By Perturbagens. If the revertants are induced by a specific agent, i.e., a perturbagen, the relevant gene or genes may be recovered even more easily. As outlined above, see, Section VI.B.2., supra, a perturbagen may be nucleic acid encoding a cell proliferation associated protein, or a protein fragment acting akin to a dominant-negative mutant that disrupts crucial protein/protein interactions involving cell proliferation genes.

In cases where revertants are based on the expression of a cell proliferation gene, or on a protein or protein fragment acting akin to a dominant-negative mutant of signal transduction pathways, the cell proliferation gene or protein/protein interaction underlying the promotion of cell growth can be determined by means of identification of the nature of the perturbagen. In most cases, one of two scenarios will apply. First, the perturbagen may be determined to be a cell proliferation gene itself. In such cases, determination of the nature of the cell proliferation gene is simply accomplished by analysis of the perturbagen product. Second, the perturbagen may act by disrupting a protein/protein interaction in a growth control pathway. In this case, two steps are required: first, the cDNA encoding the perturbagen needs to be identified and isolated. In a second step, the protein/protein interaction affected by the dominant-negative mutant is identified employing assays known in the art, suitable for the identification of protein/protein interactions such as the yeast two-hybrid system. Bartel et al., 1995, *Methods Enzymol.* 254:241–263.

Biological Function And Relevance Of The Identified Cell Proliferation Gene And Its Product. The methods of the invention described above permit the identification of highly preselected candidates for crucial components of cellular growth proliferation pathways. In order to confirm their specific biological function and relevance, these candidates are tested in suitable in vitro and in vivo assays. The design of the assays will vary depending on the growth control pathway which was targeted by a particular selection system. For example, genes identified with selection systems based on, e.g., the overexpression of a tumor suppressor may be expressed in cultured cells, e.g., NIH3T3 cells, and their effect on cell growth, DNA synthesis, focus formation, growth in soft agar, modification, e.g., phosphorylation of components or substrates in signal transduction pathways, complex formation of signal transduction components, including adapter molecules, changes in the pattern of gene expression, e.g., induction of transcription factors, including c-jun, c-fos, c-myc, etc. is determined. In vitro assays are designed to determine substrate or ligand binding, phosphorylation signal transduction molecules, etc. Further, loss of function mutations may be generated in mice (knockout mice) or transgenic mice may be produced in which the gene is ectopically expressed. Dominant-negative mutants may be engineered in mouse or in human cells. Anti-sense constructs or oligonucleotides may be employed to downregulate expression of the specific gene. In certain cases, the gene or its homologs may be studied in yeast cells.

F. Expression of the Cell Proliferation Gene in Cultured Cells

In order to express a biologically active cell proliferation gene in cultured cells, the nucleotide sequence encoding the cell proliferation gene, as identified and isolated as described in Section VI.E., supra, or a functional equivalent, is inserted into an appropriate expression vector, i.e., a vector which contains the necessary elements for the transcription and translation of the inserted coding sequence. The cell proliferation gene products as well as host cells or cell lines transfected or transformed with recombinant cell proliferation gene expression vectors can be used for a variety of purposes. These include diagnostic uses, and generating antibodies (i.e., monoclonal or polyclonal) that bind to the cell proliferation gene, as well as the identification of analogues or drugs that act on the cell proliferation gene, and for diagnostic purposes.

1. Expression Systems

Methods which are well known to those skilled in the art are used to construct expression vectors containing the cancer gene coding sequence and appropriate transcriptional/translational control signals. These methods include in vitro recombinant DNA techniques, synthetic techniques and in vivo recombination/genetic recombination. See, for example, the techniques described in Sambrock et al., supra; and Ausubel et al., 1989, *Current Protocols in Molecular Biology*, Greene Publishing Associates and Wiley Interscience, N.Y.

A variety of host-expression vector systems are utilized to express the cell proliferation gene encoding sequence. These include, but are not limited to, microorganisms such as bacteria transformed with recombinant bacteriophage DNA, plasmid DNA or cosmid DNA expression vectors containing the cell proliferation gene encoding sequence; yeast transformed with recombinant yeast expression vectors containing the cell proliferation gene encoding sequence; insect cell systems infected with recombinant virus expression vectors (e.g., baculovirus) containing the cell proliferation gene encoding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the cell proliferation gene encoding sequence; or animal cell systems infected with recombinant virus expression vectors (e.g., adenovirus, vaccinia virus) including cell lines engineered to contain multiple copies of the cell proliferation gene DNA either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage X, plac, ptrp, ptac (ptrp-lac hybrid promoter) and the like are used; when cloning in insect cell systems, promoters such as the baculovirus polyhedrin promoter are used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) are used; when cloning in mammalian cell systems, promoters derived from the genome of mammalian cells (e.g., metallothionein promoter) or from mammalian viruses (e.g., the adenovirus late promoter; the vaccinia virus 7.5K promoter) are used; when generating cell lines that contain multiple copies of the cell proliferation gene DNA SV40-, BPV- and EBV-based vectors are used with an appropriate selectable marker.

In bacterial systems a number of expression vectors are advantageously selected depending upon the use intended for the cell proliferation gene expressed. For example, when large quantities of cell proliferation gene product are to be produced for the generation of antibodies or to screen peptide libraries, vectors which direct the expression of high levels of fusion protein products that are readily purified are desirable. Such vectors include, but are not limited to, the *E. coli* expression vector pUR278 (Ruther et al., 1983, *EMBO J.* 2:1791), in which the cell proliferation gene coding sequence may be ligated into the vector in frame with the lacZ coding region so that a hybrid AS-lacZ protein is produced; pIN vectors (Inouye and Inouye, 1985, *Nucleic Acids Res.* 13:3101–3109; Van Heeke and Schuster, 1989, *J. Biol. Chem.* 264:5503–5509); and the like. pGEX vectors may also be used to express foreign polypeptides as fusion proteins with glutathione S-transferase (GST). In general, such fusion proteins are soluble and are easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review, see, *Current Protocols in Molecular Biology*, Vol. 2, 1988, Eds. Ausubel et al., Greene Publish. Assoc. & Wiley Interscience, Ch. 13; Grant et al., 1987, *Expression and Secretion Vectors for Yeast, in: Methods in Enzymology*, Eds. Wu & Grossman, 1987, Acad. Press, N.Y., Vol. 153, pp. 516–544; Glover, 1986, *DNA Cloning*, Vol. II, IRL Press, Wash., D.C., Ch. 3; and Bitter, 1987, *Heterologous Gene Expression in Yeast, Methods in Enzymology*, Eds. Berger & Kimmel, Acad. Press, N.Y., Vol. 152, pp. 673–684; and *The Molecular Biology of the Yeast Saccharomyces*, 1982, Eds. Strathern et al., Cold Spring Harbor Press, Vols. I and II.

In cases where plant expression vectors are used, the expression of the cell proliferation gene encoding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs are introduced into plant cells using Ti plasmids, Ri plasmids, plant virus vectors, direct DNA transformation, microinjection, electroporation, etc. For reviews of such techniques, see, for example, Weissbach and Weissbach, 1988, *Methods for Plant Molecular Biology*, Academic Press, NY, Section VIII, pp. 421–463; and Grierson and Corey, 1988, *Plant Molecular Biology*, 2d Ed., Blackie, London, Ch. 7–9.

An alternative expression system which can be used to express the cell proliferation gene is an insect system. In one such system, *Autographa californica* nuclear polyhidrosis virus (AcNPV) is used as a vector to express foreign genes. The virus grows in *Spodoptera frugiperda* cells. The cell proliferation gene encoding sequence may be cloned into non-essential regions (for example the polyhedrin gene) of the virus and placed under control of an AcNPV promoter (for example the polyhedrin promoter). Successful insertion of the cell proliferation gene encoding sequence results in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. See, for example, Smith et al., 1983, *J. Viol.* 46:584; U.S. Pat. No. 4,215,051.

In mammalian host cells, a number of viral based expression systems may be utilized. In cases where an adenovirus is used as an expression vector, the cell proliferation gene encoding sequence is ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the cell proliferation gene in infected hosts. See, for example, Logan and Shenk, 1984, *Proc. Natl. Acad. Sci. U.S.A.* 81:3655–3659. Alternatively, the vaccinia 7.5K promoter may be used. See, for example, Mackett et al., 1982, *Proc. Natl. Acad. Sci. U.S.A.* 79:7415–7419; Mackett et al., 1984, *J. Virol.* 49:857–864; Panicali et al., 1982, *Proc. Natl. Acad. Sci. U.S.A.* 79:4927–4931.

Specific initiation signals may also be required for efficient translation of inserted cell proliferation gene encoding sequences. These signals include the ATG initiation codon and adjacent sequences. In cases where the entire cell proliferation gene, including its own initiation codon and adjacent sequences, is inserted into the appropriate expression vector, no additional translational control signals may be needed. However, in cases where only a portion of the cell proliferation gene encoding sequence is inserted, exogenous translational control signals, including the ATG initiation codon, must be provided. Furthermore, the initiation codon must be in phase with the reading frame of the cell proliferation gene encoding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See, Bittner et al., 1987, *Methods in Enzymol.* 153:516–544.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, W138, etc.

For long-term, high-yield production of recombinant proteins, stable expression is preferred. For example, cell lines which stably express the cell proliferation gene may be engineered. Rather than using expression vectors which contain viral origins of replication, host cells are transformed with the cell proliferation gene encoding DNA controlled by appropriate expression control elements (e.g., promoter, enhancer, sequences, transcription terminators, polyadenylation sites, etc.), and a selectable marker. Following the introduction of foreign DNA, engineered cells are allowed to grow for 1–2 days in an enriched media, and then are switched to a selective media. The selectable marker in the recombinant plasmid confers resistance to the selection and allows cells to stably integrate the plasmid into their chromosomes and grow to form colonies which in turn can be cloned and expanded into cell lines.

A number of selection systems may be used, including but not limited to, the herpes simplex virus thymidine kinase (Wigler et al., 1977, *Cell* 11:223), hypoxanthine-guanine phosphoribosyltransferase (Szybalska and Szybalski, 1962, *Proc. Natl. Acad. Sci. U.S.A.* 48:2026), and adenine phosphoribosyltransferase (Lowy et al., 1980, *Cell* 22:817) genes can be employed in tk⁻, hgprt⁻ or aprt⁻ cells, respectively. Also, antimetabolite resistance can be used as the basis of selection for dhfr, which confers resistance to methotrexate (Wigler et al., 1980, *Proc. Natl. Acad. Sci. U.S.A.* 77:3567; O'Hare et al., 1981, *Proc. Natl. Acad. Sci. U.S.A.* 78:1527); gpt, which confers resistance to mycophenolic acid (Mulligan and Berg, 1981, *Proc. Natl. Acad. Sci. U.S.A.* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes. Additional selectable genes have been described, namely trpB, which allows cells to utilize indole in place of tryptophan; hisD, which allows cells to utilize histinol in place of histidine (Hartman and Mulligan, 1988, *Proc. Natl. Acad. Sci. U.S.A.* 85:8047); and ODC (ornithine decarboxylase) which confers resistance to the ornithine decarboxylase inhibitor, 2-(difluoromethyl)-DL-ornithine, DFMO (McConlogue, 1987, in: *Current Communications in Molecular Biology*, Cold Spring Harbor Laboratory ed.).

Host cells containing the coding sequence and which express the biologically active cell proliferation gene product may be identified by several general approaches, including DNA-DNA or DNA-RNA hybridization, the presence or absence of "marker" gene functions, assessment of the level of transcription as measured by the expression of cell proliferation gene mRNA transcripts in the host cell, and the detection of the gene product as measured by immunoassay or by its biological activity. These approaches are described in more detail in Section VI.D., supra.

The cell proliferation gene products can also be expressed in transgenic animals. Animals of any species, including, but not limited to, mice, rats, rabbits, guinea pigs, pigs, micropigs, goats, and non-human primates, e.g., baboons, monkeys, and chimpanzees may be used to generate transgenic animals using methods known in the art to introduce the cell proliferation associated transgene into animals to produce the founder lines of transgenic animals. Such techniques include, but are not limited to, pronuclear microinjection (Hoppe, P.C. and Wagner, 1989, U.S. Pat. No. 4,873,191); retrovirus mediated gene transfer into germ lines (Van der Putten et al., 1985, *Proc. Natl. Acad. Sci. U.S.A.* 82:6148–6152); gene targeting in embryonic stem cells (Thompson et al., 1989, *Cell* 56:313–321); electroporation of embryos (Lo, 1983, *Mol. Cell. Biol.* 3:1803–1814); and sperm-mediated gene transfer (Lavitrano et al., 1989, *Cell* 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the cell proliferation associated transgene in all their cells, as well as animals which carry the transgene in some, but not all of their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, *Proc. Natl. Acad. Sci. U.S.A.* 89:6232–6236). The regulatory sequences required for such a cell-type specific activation will depend upon the particular selected cell type, and will be apparent to those of skill in the art.

When it is desired that the cell proliferation associated transgene be integrated into the chromosomal site of the endogenous cell proliferation gene homologue, gene targeting is preferred. Briefly, when such a technique is to be utilized, vectors containing some nucleotide sequences homologous to the endogenous cell proliferation gene homologue are designed for the purpose of integrating, via homologous recombination with chromosomal sequences, into and disrupting the function of the nucleotide sequence of the endogenous cell proliferation gene. The transgene may also be selectively introduced into a particular cell type, thus inactivating the endogenous cell proliferation gene in only that cell type, by following, for example, the teaching of Gu et al. (Gu et al., 1994, *Science* 265:103–106). The regulatory sequences required for such a cell-type specific inactivation will depend upon the particular cell type of interest, and will be apparent to those of skill in the art.

Once transgenic animals have been generated, the expression of the recombinant cell proliferation gene is assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of cell type samples obtained from the animal, in situ hybridization analysis, and RT-PCR. Samples of the cell proliferation gene-expressing tissue, are evaluated immunocytochemically using antibodies specific for the cell proliferation associated transgene product.

G. Use of the Identified Cell Proliferation Gene Sequences for Diagnosis of Aberrant or Uncontrolled Expression of Cell Proliferation Gene Products Related to Cell Proliferation Disorders or Cell Proliferation Disorder Predisposition The cell proliferation gene DNAs identified with the selection systems of the present invention have a number of uses for the diagnosis of diseases resulting from their aberrant expression. For example, probes generated according to the cell proliferation gene DNA are used in hybridization assays of autopsies or biopsies to diagnose abnormalities in their expression, thereby providing a basis for a defined and targeted treatment of the disease.

A variety of methods can be employed for the diagnostic and prognostic evaluation of diseases related to aberrant expression of cell proliferation associated genes, including cancer, and for the identification of subjects having a predisposition to such disorders. Such methods may, for example, utilize reagents such as the cell proliferation gene's nucleotide sequences described in Section VI.E., supra, and antibodies directed to the cell proliferation gene product, as described, in Section VI.I, infra. Specifically, such reagents may be used, for example, for: (1) the detection of the presence of cell proliferation gene mutations, or the detection of either over- or under-expression of the cell proliferation gene's mRNA relative to the state found in normal cell activation; (2) the detection of either an over- or an under-abundance of cell proliferation gene product relative to the normal state; and (3) the detection of perturbations or abnormalities in the signal transduction pathway mediated by the cell proliferation gene product.

The methods described herein may be performed, for example, by utilizing pre-packaged diagnostic kits comprising at least one specific cell proliferation gene nucleotide sequence or antibody reagent directed to its gene product described herein, which may be conveniently used, e.g., in clinical settings, to diagnose patients exhibiting cell proliferation disorder abnormalities.

For the detection of cell proliferation gene mutations, any nucleated cell can be used as a starting source for genomic or messenger nucleic acid. For the detection of the cell proliferation gene's expression or its gene products, any cell type or tissue in which the cell proliferation gene is expressed, most typically the afflicted tissue exhibiting a disease related to uncontrolled cell proliferation, may be utilized.

Nucleic acid-based detection techniques are described in Section VI.G.1., infra. Peptide detection techniques are described in Section VI.G.2., infra.

1. Detection of the Cell Proliferation Gene and its Transcript

In one embodiment, the cell proliferation gene cDNA or fragments thereof are used as a probe to detect the expression of the cell proliferation gene mRNA. For example, sections of tissue samples may be prepared and examined by in situ hybridization with a suitable, labelled probe. Alternately, mRNA extracts may be prepared and analyzed in Northern blot analysis. Alternatively, synthetic oligonucleotides designed according to the cell proliferation gene's cDNA sequence may be generated and used as hybridization probes. Detailed description of suitable protocols can be found, for example, in Sambrook et al., *Molecular Cloning: A Laboratory Manual*, 2nd Ed., Cold Spring Harbor (1989).

In one embodiment, the level of the cell proliferation gene's expression is assayed by detecting and measuring its transcription. For example, RNA from a cell type or tissue known, or suspected to over- or under-express the cell proliferation gene, such as cancerous tissue, is isolated and tested utilizing hybridization or PCR techniques such as are described herein. The isolated cells can be derived from cell culture or from a patient. The analysis of cells taken from culture may be a necessary step in the assessment of cells to be used as part of a cell-based gene therapy technique or, alternatively, to test the effect of compounds on the expression of the cell proliferation gene. Such analyses may reveal both quantitative and qualitative aspects of the expression pattern of the cell proliferation gene, including activation or inactivation of its gene expression.

In another embodiment, probes corresponding to the cell proliferation gene sequence are employed for analysis of the genomic DNA in order to identify individuals who are predisposed for, e.g., a particular type of cancer. Predisposed individuals are then monitored on a frequent basis in order to ensure early diagnosis of potential disease, which drastically increases the likelihood of therapeutical success. Detailed description of suitable protocols for such Southern blot analysis can be found, among other places, in Sambrook et al., *Molecular Cloning: A Laboratory Manual*, 2nd Ed., Cold Spring Harbor (1989).

Hybridization probes for Northern blot, Southern blot, and in situ hybridization may be labeled by a variety of reporter groups, including radionuclides such as $^{32}P$, $^{35}S$, and $^{3}H$ (in the case of in situ hybridization), or enzymatic labels, such as alkaline phosphatase, coupled to the probe via avidin/biotin coupling systems, and the like. The labeled hybridization probes may be prepared by any method known in the art for the synthesis of DNA and RNA molecules. See, Section VI.H., infra. An additional use for nucleic acid hybridization probes involves their use as primers for polymerase chain reaction (PCR). PCR is described in detail in U.S. Pat. Nos. 4,965,188, 4,683,195, and 4,800,195.

In still other embodiments, mutations within the cell proliferation gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving gene structure, including point mutations, insertions, deletions and chromosomal rearrangements. Such assays include, but are not limited to, Southern analyses, single stranded conformational polymorphism analyses (SSCP), and PCR analyses.

Diagnostic methods for the detection of cell proliferation gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, under conditions favorable for the specific annealing of these reagents to their complementary sequences within the cell proliferation gene. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any, is then detected. Using such a detection system, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents are easily removed. Detection of the remaining, annealed, labeled cell proliferation gene's nucleic acid reagents is accomplished using standard techniques well-known to those in the art. The cell proliferation gene sequences to which the nucleic acid reagents have annealed is compared to the annealing pattern expected from a normal gene sequence in order to determine whether a gene mutation is present.

Alternative diagnostic methods for the detection of the cell proliferation gene's specific nucleic acid molecules, in patient samples or other appropriate cell sources, may involve their amplification, e.g., by PCR (the experimental embodiment set forth in Mullis, K. B., 1987, U.S. Pat. No. 4,683,202, see, supra), followed by the detection of the amplified molecules using techniques well known to those of skill in the art. The resulting amplified sequences can be compared to those which would be expected if the nucleic acid being amplified contained only normal copies of the cell proliferation gene in order to determine whether a gene mutation exists.

Additionally, well-known genotyping techniques can be performed to identify individuals carrying mutations in the cell proliferation gene. Such techniques include, for example, the use of restriction fragment length polymorphisms (RFLPs), which involve sequence variations in one of the recognition sites for the specific restriction enzyme used.

2. Detection of the Cell Proliferation Gene Product

Antibodies directed against wild type or mutant cell proliferation gene products or conserved variants or peptide fragments thereof, may also be used as cell growth disorder diagnostics and prognostics, as described herein. Such diagnostic methods, may be used to detect abnormalities in the level of the gene's expression, or abnormalities in the structure and/or temporal, tissue, cellular, or subcellular location of its gene product, and may be performed in vivo or in vitro, such as, for example, on biopsy tissue.

The tissue or cell type to be analyzed will generally include those which are known, or suspected, to aberrantly express the cell proliferation gene, such as, for example, cancerous tissue. The protein isolation methods employed herein may, for example, be such as those described in Harlow and Lane (Harlow, E. and Lane, D., 1988, *"Antibodies: A Laboratory Manual"*, Cold Spring Harbor Laboratory Press, Cold Spring Harbor, N.Y.). The isolated cells can be derived from cell culture or from a patient. The analysis of cells taken from culture may be a necessary step in the assessment of cells that are used as part of a cell-based gene therapy technique or, alternatively, to test the effect of compounds on the expression of the cell proliferation gene.

For example, antibodies, or fragments of antibodies useful in the present invention, such as those described in Section VI.I, infra, may be used to quantitatively or qualitatively detect the presence of the cell proliferation gene products or conserved variants or peptide fragments thereof. This can be accomplished, for example, by immunofluorescence techniques employing a fluorescently labeled antibody (see, this Section, infra) coupled with light microscopic, flow cytometric, or fluorimetric detection.

The antibodies (or fragments thereof) or fusion or conjugated proteins useful in the present invention may, additionally, be employed histologically, as in immunofluorescence, immunoelectron microscopy or non-immuno assays, for in situ detection of the cell proliferation gene products or conserved variants or peptide fragments thereof, or for catalytic subunit binding (in the case of labeled catalytic subunit fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the cell proliferation gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for cell proliferation gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying the cell proliferation gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled antibody or fusion protein. The solid phase support may then be washed with the buffer a second time to remove unbound antibody or fusion protein. The amount of bound label on solid support is then detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to readily ascertain the same.

The binding activity of a given lot of antibody or fusion protein is determined according to well known methods. Those skilled in the art will be able to readily determine operative and optimal assay conditions.

With respect to antibodies, one of the ways in which the antibody can be detectably labeled is by linking the same to an enzyme and use in an enzyme immunoassay (EIA) (Voller, 1978, *Diagnostic Horizons* 2:1–7, Microbiological Associates Quarterly Publication, Walkersville, Md.); Voller et al., 1978, *J. Clin. Pathol.* 31:507–520; Butler, 1981, *Meth. Enzymol.* 73:482–523; Maggio, E. (ed.), 1980, *Enzyme Immunoassay*, CRC Press, Boca Raton, Fla.,; Ishikawa et al., (eds.), 1981, *Enzyme Immunoassay*, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect the cell proliferation gene product through the use of a radioimmunoassay (RIA) (see, for example, Weintraub, B., *Principles of Radioimmunoassays*, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

H. Use of the Identified Cell Proliferation Gene Sequences for Development of Antisense Approaches and Ribozymes Also within the scope of the subject invention is the use of oligonucleotide or oligoribonucleotide sequences comprising antisense DNA or RNA molecules or ribozymes that function to inhibit the translation of the cell proliferation gene mRNA. For example, antisense DNA or RNA molecules act to directly block the translation of the cell proliferation gene by binding to the targeted mRNA and thus preventing protein translation.

Ribozymes are enzymatic RNA molecules capable of catalyzing the specific cleavage of RNA. The mechanism of ribozyme action appears to involve site specific hybridization of the ribozyme molecule to complementary sequences of the target RNA, followed by a endonucleolytic cleavage. In one embodiment of the invention, ribozyme molecules are engineered that specifically catalyze endonucleolytic cleavage of mRNA of the cell proliferation genes identified with the selection systems of the invention.

Suitable target sites for ribozyme activity are identified by first scanning the target molecule for potential ribozyme cleavage motifs, second by evaluating the structural features of the about 15 to 25 amino acids corresponding to the region of the target molecule containing the identified cleavage recognition site. Further, the suitability of the candidate targets may also be evaluated by testing their accessibility to hybridization with complementary oligonucleotides, using ribonuclease protection assays. Bordonaro et al., 1994, *Biotechniques* 16:428–430.

The labeled hybridization probes, see, Section VI.G.1., supra, antisense DNA and RNA oligonucleotides and ribozymes of the subject invention are prepared by any method known in the art for the synthesis of DNA and RNA molecules. For example, oligonucleotides may be synthesized chemically using commercially available DNA or RNA synthesizers like machines sold by Applied Biosystems. Alternatively, RNA molecules may be generated by in vitro and in vivo transcription of DNA sequences encoding the antisense RNA molecule. Such DNA sequences may be incorporated into a wide variety of vectors which comprise suitable RNA polymerase promoters such as the T3, T7, or the SP6 polymerase promoters. Alternatively, antisense cDNA constructs that synthesize antisense RNA constitutively or inducibly, may be introduced stably into cell lines.

Various modifications to the DNA and RNA molecules may be introduced as a means of increasing the intracellular stability and half-life. For example, flanking sequences of ribo- or deoxy-nucleotides may be added to the 5' and/or 3' ends of the molecule, or phosphorothioate or 2' O-methyl rather than phosphodiester linkages may be used within the oligonucleotide backbone. Xu et al., 1996, *Nucleic Acid Res.* 24:1602–1607.

I. Generation and Use of Cell Proliferation Gene Antibodies

Various procedures known in the art may be used for the production of antibodies to epitopes of the recombinantly produced cell proliferation genes identified and isolated employing the selection systems of the present invention. Such antibodies include but are not limited to polyclonal, monoclonal, chimeric, single chain, Fab fragments and fragments produced by an Fab expression library. Such antibodies may be useful, e.g., as diagnostic or therapeutic agents. As therapeutic agents, neutralizing antibodies, i.e., those which compete for binding with a ligand, substrate or adapter molecule, or interfering with the cell proliferation genes activity, are of especially preferred interest.

For use as diagnostic agents, monoclonal antibodies that bind to the cell proliferation gene are radioactively labeled allowing detection of their location and distribution in the body after injection. Radioactivity tagged antibodies may be used as a non-invasive diagnostic tool for imaging in vivo the presence of a tumors and metastases associated with the expression of said cell proliferation gene.

Immunotoxins may also be designed which target cytotoxic agents to specific sites in the body. For example, high affinity monoclonal antibodies may be covalently complexed to bacterial or plant toxins, such as diphtheria toxin, abrin, or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate cells expressing the cell proliferation gene.

For the production of antibodies, various host animals are immunized by injection with the cell proliferation gene protein including, but not limited to, rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to the cell proliferation gene may be prepared using any technique which provides for the production of antibody molecules by continuous cell lines in culture. These include, but are not limited to, the hybridoma technique originally described by Kohler and Milstein, 1975, *Nature* 256:495–497, the human B-cell hybridoma technique (Kosbor et al., 1983, *Immunology Today* 4:72; Cote et al., 1983, *Proc. Natl. Acad. Sci. U.S.A.* 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cell proliferation gene-specific single chain antibodies.

Antibody fragments which contain specific binding sites of the cell proliferation gene may be generated by known techniques. For example, such fragments include, but are not limited to, $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science* 246:1275–1281) to allow rapid and easy identification of monoclonal Fab fragments with the desired specificity to the cell proliferation gene.

J. Use of Revertant Cells or the Isolated Cell Proliferation Genes for the Identification of Compounds Useful for the Treatment of Disease Related to Uncontrolled Cell Proliferation 1. Identification of Compounds The revertant cells identified using the selection system process of the invention, may be used directly, i.e., without isolation of the relevant cell proliferation gene, for the identification and isolation of compounds inhibiting aberrant cell proliferation. Alternatively, the cell proliferation genes identified by the process of the invention may be isolated and used for in vitro or in vivo assays for the identification and isolation of compounds specifically interfering with their activity.

More specifically, the identified revertant cells may be exposed to chemical compounds or compound libraries, and compounds exhibiting growth inhibition may be identified. Alternatively, the identified cell proliferation genes may be expressed in suitable expression systems, designed to allow for high-throughput testing of compounds from any source to identify molecules having an inhibitory effect on the cell proliferation genes.

Nucleotide sequences encoding the cell proliferation genes identified and isolated using the selection systems of the invention may be used to produce the corresponding purified protein using well-known methods of recombinant DNA technology. Among the many publications that teach methods for the expression of genes after they have been isolated is *Gene Expression Technology, Methods and Enzymology* Vol.:185, edited by Goeddel, Academic Press, San Diego, Calif. (1990).

The cell proliferation genes may be expressed in a variety of host cells, either prokaryotic or eukaryotic. In many cases, the host cells would be eukaryotic, more preferably host cells would be mammalian. Host cells may be from species either the same or different than the species from which the cell proliferation gene encoding nucleotide sequences are naturally present, i.e., endogenous. Advantages of producing the cell proliferation genes by recombinant DNA technology include obtaining highly enriched sources of the proteins for purification and the availability of simplified purification procedures. Methods for recombinant production of proteins are generally very well established in the art, and can be found, among other places in Sambrock et al., supra.

In one embodiment of the invention, cells transformed with expression vectors encoding the cell proliferation gene are cultured under conditions favoring expression of the cell proliferation gene sequence and the recovery of the recombinantly-produced protein from the cell culture. A cell proliferation gene produced by a recombinant cell may be secreted or may be contained intracellularly, depending on the nature of the cell proliferation gene and the particular genetic construction used. In general, it is more convenient to prepare recombinant proteins in secreted form. Purification steps will depend on the nature of the production and the particular cell proliferation gene produced. Purification methodologies are well established in the art; the skilled artisan will know how to optimize the purification conditions. General protocols of how to optimize the purification conditions for a particular protein can be found, among other places, in Scopes in: *Protein Purification: Principles and Practice,* 1982, Springe-Verlag New York, Heidelberg, Berlin.

In addition to recombinant production, cancer peptide fragments may be produced by direct peptide synthesis using solid-phase techniques. See, Stewart et al., *Solid-Phase Peptide Synthesis* (1969), W. H. Freeman Co., San Francisco; and Merrifield, 1963, *J. Am. Chem. Soc.* 85:2149–2154.

In vitro polypeptide synthesis may be performed using manual techniques or by automation. Automated synthesis may be achieved, for example, using Applied Biosystems 431A Peptide Synthesizer (Foster City, Calif.) following the instructions provided in the instruction manual supplied by the manufacturer.

In one embodiment of the invention, the cell proliferation genes and/or expressing cell lines expressing the cell proliferation gene are used to screen for antibodies, peptides, organic molecules or other ligands that act as agonist or antagonists of the cell proliferation gene activity. For example, antibodies capable of interfering with the activity, e.g., enzymatic activity of the cell proliferation gene, or with its interaction with a ligand, adapter molecule, or substrate are used to inhibit the cell proliferation gene function. In cases where amplification of the cell proliferation gene function is desired, antibodies which mimic, e.g., a ligand, an adapter molecule or substrate of the corresponding the signal transduction pathway may be developed. Obviously, if desired, antibodies may be generated which modify the activity, function, or specificity of the cell proliferation gene.

Alternatively, screening of peptide libraries or organic compounds with recombinantly expressed cell proliferation gene protein or cell lines expressing the cell proliferation gene may be useful for identification of therapeutic molecules that function by inhibiting, enhancing, or modifying its biological activity.

Synthetic compounds, natural products, and other sources of potentially biologically active materials can be screened in a number of ways. The ability of a test compound to inhibit, enhance or modulate the function of the cell proliferation gene may be determined with suitable assays measuring the cell proliferation gene function. For example, responses such as its activity, e.g., enzymatic activity, or its ability to bind its ligand, adapter molecule or substrate may be determined in in vitro assays. Cellular assays may be developed to monitor a modulation of second messenger production, changes in cellular metabolism, or effects on cell proliferation. These assays may be performed using conventional techniques developed for these purposes. Finally, the ability of a test compound to inhibit, enhance or modulate the function of the cell proliferation gene will be measured in suitable animal models in vivo. For example, mouse models will be used to monitor the ability of a compounds to inhibit the development of solid tumors, or effect reduction of the solid tumor size.

In one embodiment of the invention, random peptide libraries consisting of all possible combinations of amino acids attached to a solid phase support are used to identify peptides that are able to interfere with the function of the cell proliferation gene. For example, peptides may be identified binding to a ligand-, adapter molecule- or substrate binding site of a given cell proliferation gene or other functional domains of the cell proliferation gene, such as an enzymatic domain. Accordingly, the screening of peptide libraries may result in compounds having therapeutic value as they interfere with its activity.

Identification of molecules that are able to bind to the cell proliferation gene may be accomplished by screening a peptide library with recombinant soluble cell proliferation gene protein. Methods for expression and purification of the selected cell proliferation genes are described in Section VI.F., supra, and may be used to express recombinant full length cell proliferation gene protein or fragments thereof, depending on the functional domains of interest.

In order to identify and isolate the peptide/solid phase support that interacts and forms a complex with the cell proliferation gene, it is necessary to label or "tag" the cell proliferation gene molecule or fragment thereof. For example, the cell proliferation gene may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to the cell proliferation gene may be performed using techniques that are routine in the art.

In addition to using soluble cell proliferation gene molecules or fragments thereof, in another embodiment, peptides that bind to the cell proliferation gene may be identified using intact cells. The use of intact cells is preferred for use with cell proliferation genes which comprise cell surface receptors, which require the lipid domain of the cell membrane to be functional. Methods for generating cell lines expressing the cell proliferation genes identified with the selection systems of the invention are described in Section VI.F., supra. The cells used in this technique may be either live or fixed cells. The cells are incubated with the random peptide library and will bind to certain peptides in the library. The so formed complex between the target cells and the relevant solid phase support/peptide may be isolated by standard methods known in the art, including differential centrifugation.

As an alternative to whole cell assays for membrane bound receptors or receptors that require the lipid domain of the cell membrane to be functional, the receptor molecules can be reconstituted into liposomes where a label or "tag" can be attached.

In another embodiment, cell lines that express the cell proliferation gene or, alternatively isolated cell proliferation gene protein or fragments thereof, are used to screen for molecules that inhibit, enhance, or modulate the cell proliferation gene activity or signal transduction. Such molecules may include small organic or inorganic compounds, or other molecules that effect the cell proliferation gene activity or that promote or prevent the complex formation with its ligand, adapter molecules, or substrates. Synthetic compounds, natural products, and other sources of potentially biologically active materials can be screened in a number of ways, which are generally known by the skilled artisan.

For example, the ability of a test molecule to interfere with the cell proliferation gene function may be measured using standard biochemical techniques. Alternatively, cellular responses such as activation or suppression of a catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Further, effects on the cell proliferation gene function may, via signal transduction pathways, affect a variety of cellular processes. Cellular processes under the control of the cell proliferation gene signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition and, blocking of differentiation or cell death. The qualitative or quantitative observation and measurement of any of the described cellular processes by techniques known in the art may be advantageously used as a means of scoring for signal transduction in the course of screening.

Various technologies may be employed for the screening, identification, and evaluation of compounds which interact with the cell proliferation genes of the invention, which compounds may affect various cellular processes under the control of said cell proliferation gene.

For example, the cell proliferation gene or a functional derivative thereof, in pure or semi-pure form, in a membrane preparation, or in a whole live or fixed cell is incubated with the compound. Subsequently, under suitable conditions, the effect of the compound on the cell proliferation gene function is scrutinized, e.g., by measuring its activity, or its signal transduction, and comparing the activity to that of the cell proliferation gene, incubated under same conditions, without the compound, thereby determining whether the compound stimulates or inhibits the cell proliferation gene's activity.

In addition to the use of whole cells expressing the cell proliferation gene for the screening of compounds, the invention also includes methods using soluble or immobilized cell proliferation gene protein. For example, molecules capable of binding to the cell proliferation gene may be identified within a biological or chemical preparation. For example, the cell proliferation gene, or functional fragments thereof, e.g., fragments containing a specific domain of interest, is immobilized to a solid phase matrix, subsequently a chemical or biological preparation is contacted with the immobilized cell proliferation gene for an interval sufficient to allow the compound to bind. Any unbound material is then washed away from the solid phase matrix, and the presence of the compound bound to the solid phase is detected, whereby the compound is identified. Suitable means are then employed to elute the binding compound.

2. Small Molecule Displacement Assay

In a specific embodiment of the invention a system has been developed for assessing protein-protein interactions and their inhibition in a cell in vivo, e.g., a fungal, bacterial, mammalian cell, or in vitro. Those systems, referred to as small molecule displacement assays, can be used to screen libraries of small molecules to identify specific compounds that disrupt such protein-protein interaction.

The small molecule displacement assay has several advantages over traditional assays used for the identification of small molecule inhibitors. First, if the assay is performed in vivo, each compound must be able to penetrate the cell membrane to carry out its disruptive activity, and would therefore be preselected for membrane permeability, which is a desirable or even crucial pharmacological property. Moreover, the screen has general applicability since it can be used against any protein-protein interaction which can be recapitulated within a cell. Furthermore, the screen is efficient because the cells can be gridded out in wells into which compounds are applied, either individually or in pools, and the reporter construct can be assayed independently in each well. The assay might consist of a colorimetric output to report the presence or absence of the interaction, which may be performed in vivo or in vitro, or an in vivo cell growth assay.

Generally, in a first step, the protein-protein interaction is determined or verified, and in a second step, inhibitors of the interaction are identified.

Assays For The Identification And Determination Of Protein-Protein Interactions. Any method suitable for detecting protein-protein interactions may be employed for identifying intracellular proteins that interact with the cell proliferation gene product. Among the traditional methods which may be employed are co-immunoprecipitation, crosslinking and co-purification through gradients or chromatographic columns of cell lysates or proteins obtained from cell lysates to identify proteins in the lysate that interact with the cell proliferation gene product. For these assays, the cell proliferation gene product used can be a full length gene product, or a truncated peptide. Once isolated, such an interacting protein can be identified and can, in turn, be used, in conjunction with standard techniques, to identify proteins with which it interacts. For example, at least a portion of the amino acid sequence of an intracellular protein which interacts with cell proliferation gene product, can be ascertained using techniques well known to those of skill in the art, such as via the Edman degradation technique. (See, e.g., Creighton, 1983, *"Proteins: Structures and Molecular Principles"*, W.H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation and screening of oligonucleotide mixtures are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular proteins interacting with the cell proliferation gene product. These methods include, for example, probing expression libraries, in a manner similar to the well known technique of antibody probing of λgt11 libraries, using cell proliferation gene protein, or cell proliferation gene derived peptide or fusion protein, e.g., a domain fused to a marker (e.g., an enzyme, fluor, luminescent protein, or dye), or an Ig-Fc domain.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding the cell proliferation gene product, or a fragment or fusion protein thereof, and the other plasmid consists of nucleotides encoding the transcription activator protein's activation domain fused to a cDNA encoding an unknown protein or the presumably interacting protein of interest (e.g., the perturbagen) which has been recombined into this plasmid (or can be a part of a cDNA library). The DNA-binding domain fusion plasmid and the plasmid encoding the presumably interacting protein (or the cDNA library) are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to verify any protein-protein interaction identified by the present invention using the perturbagen approach, but also to screen activation domain libraries for proteins that interact with the "bait" gene product. By way of example, and not by way of limitation, the cell proliferation gene product may be used as the bait gene product. Total genomic or cDNA sequences are fused to the DNA encoding an activation domain. This library and a plasmid encoding a hybrid of a bait cell proliferation gene product gene product fused to the DNA-binding domain are cotransformed into a yeast reporter strain, and the resulting transformants are screened for those that express the reporter gene. For example, and not by way of limitation, a bait cell proliferation gene sequence, such as the open reading frame of the cell proliferation gene product or a domain thereof, is cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait cell proliferation gene product are to be detected can be made using methods routinely practiced in the art. According to the particular system described herein, for example, the cDNA fragments can be inserted into a vector such that they are translationally fused to the transcriptional activation domain of GAL4. This library can be co-transfected along with the bait cell proliferation gene product gene-GAL4 fusion plasmid into a yeast strain which contains a lacZ gene driven by a promoter which contains GAL4 activation sequence. A cDNA encoded protein, fused to a GAL4 transcriptional activation domain, that interacts with bait cell proliferation gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait cell proliferation gene-interacting protein using techniques routinely practiced in the art.

Small Molecule Displacement Assay to Identify inhibitors of the Protein-Protein Interaction. The macromolecules that interact with the cell proliferation gene product are referred to, for purposes of this discussion, as "binding partners". These binding partners are likely to be involved in the cell proliferation gene product signal transduction pathway, and therefore, in the role of the cell proliferation gene product's cell activation regulation. Therefore, it is desirable to identify compounds that interfere with or disrupt the interaction of such binding partners with the cell proliferation gene product which may be useful in regulating the activity of the cell proliferation gene product and thus control cell proliferation disorders associated with the cell proliferation gene product's activity.

The basic principle of the assay systems used to identify compounds that interfere with the interaction between the cell proliferation gene product and its binding partner or partners involves preparing a reaction mixture containing cell proliferation gene product, polypeptide, peptide or fusion protein, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the cell proliferation gene product and its binding partner. Control reaction mixtures are incubated without the test compound or with a placebo. The formation of any complexes between the cell proliferation gene product and the binding partner is then detected. The formation of a complex in the control reaction, but not in the reaction mixture containing the test compound, indicates that the compound interferes with the interaction of the cell proliferation gene product and the interactive binding partner. Additionally, complex formation within reaction mixtures containing the test compound and normal cell proliferation gene product may also be compared to complex formation within reaction mixtures containing the test compound and a mutant cell proliferation gene product. This comparison may be important in those cases wherein it is desirable to identify compounds that disrupt interactions of mutant but not normal cell proliferation gene products.

The assay for compounds that interfere with the interaction of the cell proliferation gene product and binding partners can be conducted in a heterogeneous or homogeneous format. Heterogeneous assays involve anchoring either the cell proliferation gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the cell proliferation gene product and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the cell proliferation gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the cell proliferation gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes are identified.

In an alternate embodiment of the invention, a homogeneous assay can be used. In this approach, a preformed complex of the cell proliferation gene product and the interactive binding partner is prepared in which either the cell proliferation gene product or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt cell proliferation gene product/intracellular binding partner interaction are identified.

Small Molecule Displacement Assay Following Induction of Revertants Using Perturbagens. In a particular embodiment of the invention, following isolation of the perturbagen sequence, it is relatively straightforward to define its target in the cell (assuming the target is a cellular protein) using yeast two-hybrid analysis. In one formulation of the experiment, the perturbagen is fused to the GAL4 DNA binding domain and introduced into HIS3-yeast cells. A second fusion construct is also introduced that contains the GAL4 activation domain fused to a random-primed library of cDNA inserts, preferably constructed using mRNA from the cell originally used to define the perturbagen. Selection for HIS prototropy (expression of a HIS3 gene under GAL4 control) and lacz expression (also under GAL4 control) permits identification of sequences from the library that provide reconstitution of GAL4 transcriptional activity; that is, the presence of the perturbagen/DNA binding domain fusion along with the GAL4 activation domain fusion in the same cell results in GAL4 function. This result is normally obtained when the perturbagen and a sequence from the cDNA library encode proteins that interact, bridging the two halves of the bisected GAL4 factor. Further tests can be performed, if desired, to ensure that the library sequence is indeed the binding partner (i.e., the target) of the perturbagen in vivo.

Once the perturbagen and its target are identified, it is possible to reconfigure the two-hybrid interaction so that screens for small molecules can be undertaken. Such screens take advantage of the protein-protein interaction between the perturbagen and its target. They seek out small molecules that are capable of displacing the protein-protein interaction. Technically, such a screen could be carried out in yeast cells, in mammalian cells in which the interaction has been reconstituted, or, perhaps best of all, in a test tube. Such a screen is configured by fusing one of the binding partners (e.g., the perturbagen) to a convenient reporter molecule such as Green Fluorescent Protein (GFP). The other binding partner (e.g., the target) is fused to a second protein that can be absorbed onto a solid support via a biotin bridge or an antibody or some other ligand. The interaction between the perturbagen and its target must be maintained in the new fusion setting. The release of GFP fluorescence signal from the solid support (i.e., into the supernatant) is then detected after addition of test compounds. Compounds that are able to displace the GFP/perturbagen fusion are candidates for perturbagen mimics. Some of these may bind the perturbagen, while others may bind the target. These two classes are readily distinguished by subsequent tests with the perturbagen and the target.

In general, the displacement assay must utilize a reporter construct in the cell that is not too sensitive to distances or geometries between the two protein partners. It can be applied in numerous different cell systems, a few examples are described in the following.

Yeast. The traditional two-hybrid system in yeast may be applied in both the GAL4 version and the lexA formulation. Bartel et al., 1995, *Methods Enzymol.* 254:241–263; Mendelsohn et al., 1994, *Curr. Opin. Biotechnol.* 5:482–486. Both systems take advantage of the bipartite nature of yeast transcription factors. The DNA binding component can be separated from the activation component and each fused to different proteins. If the proteins interact strongly enough with each other, a functional transcription factor is reconstituted and the reporter gene(s) are turned on. In the GAL4 version, the reporters are HIS3 and lacz. These genes are engineered to contain GAL4 binding sites upstream in a suitable position to provide activation if and only if an activation domain is also supplied, either directly or via a protein-protein interaction. HIS3-positive cells are selected for in a HIS3-mutant strain permitting growth selection. Lacz serves as a calorimetric, reasonably quantitative, independent measure of reconstituted GAL4 activity.

*E. Coli.* In bacteria, several reporter systems can be envisioned. These might involve Nut sites that function only when the DNA binding component is fused to the Nut protein anti-terminating sequences. Alternatively, the bipartite nature of the lambda phage repressor (cI) could be used in a way similar to the yeast transcriptional system. In this case, however, a protein-protein interaction would reconstitute a repressor of transcription, not an activator. Thus, when the process is disrupted, transcription ensues.

Mammalian Cells. In mammalian cells, a system similar to the yeast two hybrid system is developed, because the transcription process is relatively similar. An Upstream Activator Sequence (UAS) could be positioned upstream of a reporter gene such as Green Fluorescent Protein or lacz so that a reconstituted protein-protein interaction brought in the domain from the reporter gene results in its expression. Alternatively, the function of an adapter protein is replaced by a two-hybrid protein interaction.

Similar systems in other fungal, bacterial, or mammalian cells are contemplated.

3. Source of Candidate Test Compounds

The test compounds employed for such assays are obtained from any commercial source, including Aldrich (1001 West St. Paul Ave., Milwaukee, Wis. 53233), Sigma Chemical (P.O. Box 14508. St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the assay cascade of the invention, including microbial, fungal or plant extracts.

a. Indications for the Use of Compounds Interfering with the Cell Proliferation Genes of the Invention The compounds identified by the methods of the present invention are modulators of a cell proliferation activity in general, or a cell proliferation gene in particular. As such, the compounds produced by the processes and assays of the invention are useful for the treatment of disease related to aberrant, uncontrolled or inappropriate cell proliferation.

A large number of disease states involve excess or diminished cell proliferation. Generally, many of these diseases may be treated with DNA sequences, proteins, or small molecules that influence cell proliferation. In some instances the goal is to stimulate proliferation; in others, to prevent or inhibit proliferation of cells. The list of diseases directly involving cell growth includes, but is not limited to, cancer, psoriasis, inflammatory diseases, such as rheumatoid arthritis, restenosis, immunological activation or suppression, including tissue rejection, neurodegeneration or expansion of neuronal cells and viral infection.

Accordingly, pharmaceutical compositions comprising a therapeutically effective amount of a compound identified by the methods of the invention will be useful for the treatment of diseases driven by unregulated or inappropriate cell proliferation, including cancer, such as glioma, melanoma, Kaposi's sarcoma, psoriasis, hemangioma and ovarian, breast, lung, pancreatic, prostate, colon and epidermoid cancer, rheumatoid arthritis, psoriasis, restenosis, immunological activation or suppression, including tissue rejection, neurodegeneration or expansion of neuronal cells.

K. Formulations/Route of Administration

The identified compounds can be administered to a human patient alone or in pharmaceutical compositions where they are is mixed with suitable carriers or excipient(s) at therapeutically effective doses to treat or ameliorate a variety of disorders. A therapeutically effective dose further refers to that amount of the compound sufficient to result in amelioration of symptoms as determined in a decrease of cell proliferation. Techniques for formulation and administration of the compounds of the instant application may be found in "Remington's Pharmaceutical Sciences," Mack Publishing Co., Easton, Pa., latest edition.

1. Routes of Administration.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer a compound of the invention in a local rather than systemic manner, for example, via injection of the compound directly into a solid tumor, often in a depot, or in a sustained release formulation.

Furthermore, one may administer the drug via a targeted drug delivery system, for example, in a liposome coated with tumor-specific antibody. The liposomes will be targeted to and taken up selectively by the tumor.

2. Composition/Formulation

The pharmaceutical compositions of the present invention may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the cell proliferation inhibiting compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

3. Effective Dosage.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the cell proliferation activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred.

The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1 p1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include inhibition of cell proliferation, treatment of a tumor, treatment of arthritis, and the like.

The following examples for the generation and use of the selection systems of the invention are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VII. EXAMPLES

A. Example 1

Arrest of Melanoma Cells by Expression of P16

In this example, the generation of a growth-arrested melanoma cell line is described as a selection system of the present invention. The obtained growth-arrested melanoma cell line may be used for the selection and isolation of growth-proficient revertants. Analysis of these revertants may result in the identification and isolation of novel cell proliferation genes related to the development of diseases related to unregulated or inappropriate cell proliferation, for example, cancer.

Figure 3A:
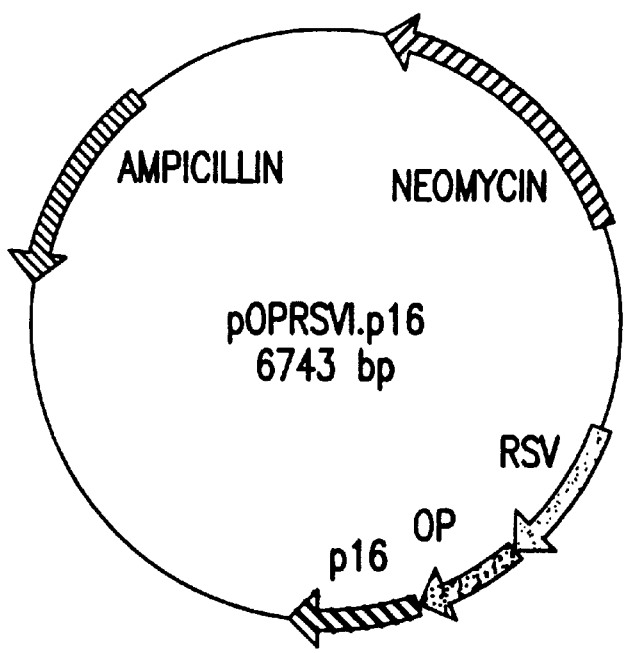
FIG. 3 depicts the pOPRSVI.p16 plasmid, a means of controlling p16 tumor suppressor protein expression in cell lines.
Figure 3B:
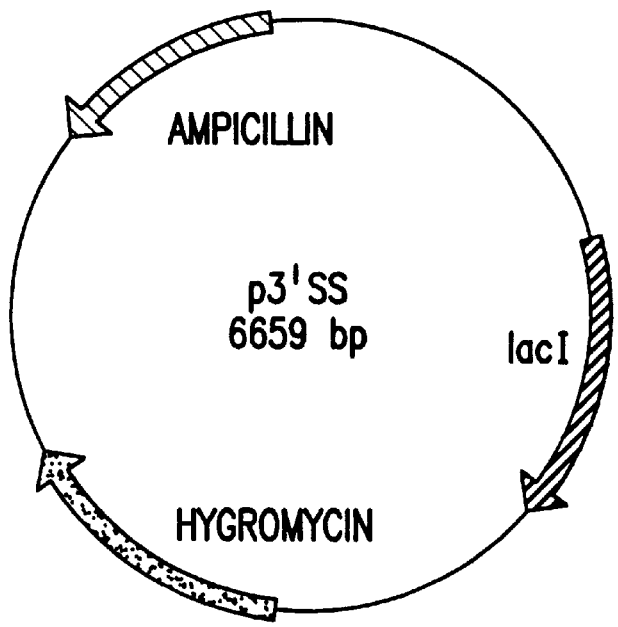

The melanoma cell line HS294T, which lacks endogenous p16, was used to create a cell that could be forced into G0/G1 arrest by introduction of the inducible p16 expression construct pOPRSVI.p16 (FIG. 3) into the cells. The promotor of the inducible p16 construct contains sequences from the Rous Sarcoma Virus (RSV) long terminal repeat (LTR) that act as a potent transcriptional initiator located upstream of the complete p16 coding sequence. Between the p16 translational start site and the RSV LTR are operator sequences derived from the *E. coli* lac operon. These sequences are sufficient for binding of the lac repressor. In the presence of functional lac repressor, transcription from the RSV LTR is dramatically reduced by the lac operator sequences. However, when IPTG is added to the culture media, the lac repressor molecules are prevented from blocking the transcription of p16; p16 mRNA is synthesized and p16 protein is produced.

As a consequence, the cells, termed HS294T/p16$^+$, respond to IPTG by induction of p16 and cell cycle arrest. Death of arrested HS294T/p16$^+$ cells after addition of IPTG occurred over a period of several days during the second week of arrest. By day fifteen (15), no viable cells were present and the vast majority of the adherent cells had disappeared from the bottom of the culture dish.

B. Example 2

Selection of Growth-Proficient Revertants

In this example, the selection of growth-proficient generated as revertants derived from the growth suppressed H2594T/p16$^+$ melanoma cells generated as described in Example 1, supra, is described. Further analysis of the revertants will reveal the identity of cell proliferation genes useful for the diagnosis and prognosis of diseases related to uncontrolled or inappropriate cell proliferation, and for the development of targeted drugs for the treatment of disease related to uncontrolled cell proliferation.

To select revertants from the population of p16-arrested cells, HS294T/p16$^+$ cells were plated in microtiter wells at a density of 2000 cells/well in the presence of IPTG. As a control, parental HS294T cells that continue to grow in the presence of IPTG were seeded at different densities among arrested HS294T/p16+ cells in a separate set of microtiter wells. As expected, these wells gave rise to growing clones of cells that spread over the well bottom.

By day twenty (20) after plating, 11/96 microtiter wells clearly contained growing cells. Assuming that a single progenitor cell spawned the colony in each of the eleven wells, this implies a reversion rate of approximately one per 20,000 arrested cells (11/96(2000)).

Materials And Methods. The melanoma cell line HS294T was engineered to contain an IPTG-inducible p16 gene in the PopRSV vector (Stratagene, San Diego, Calif.) as described by Stone et al, 1996, Cancer Res., in press. The resulting cell line, HS294T/p16, was arrested by addition of 0.1 mM IPTG after subculturing 2,000 cells per well of a 96-well culture plate (Falcon). Fresh medium (DMEM, nonessential amino acids, glutamine (2 mM), sodium pyruvate (100 mg/ml), hygromycin (30 µg,ml), geneticin (34 µg/ml), IPTG (0.1 mM) was added every four (4) to five (5) days. After twenty (20) days, eleven (11) wells were judged to contain growing cells, six (6) of which survived subcloning. These revertant growth-proficient cells were grown up in flasks for subsequent analysis in the absence of IPTG.

Cells from the eleven positive wells were transferred to larger culture dishes. The cells were allowed to grow in the absence of IPTG to mitigate against toxicity of the IPTG which over long periods of exposure impairs HS294T viability. The value of this precaution was confirmed by subcloning the parental HS294T control cells in the presence of IPTG, a process that killed the cells. Despite IPTG withdrawal, only six revertant lines survived the transfer procedure. These lines were grown up and characterized in several ways.

C. Example 3
Characterization of the Revertants

To ensure that the revertant cell lines of Example 2 were still resistant to IPTG-induced p16, the lines were returned to IPTG-containing media. In contrast to the original HS294T/p16+ cells which enter $G_0/G_1$ arrest within twenty four (24) hours, all six revertant cell lines continued to grow. The percentages of cells in $G_0/G_1$ in the presence and absence of IPTG were measured and compared to the distributions in various control cell lines. The revertant lines had largely similar growth profiles to the parental lines. The rev4 and rev6 lines appeared to have slightly lower $G_1/G_2$ ratios indicating more significant changes to the cellular signal transduction (TABLE III) compared to the parentel H5294T/p16+ line. The rev1 line appeared to possess some residual p16 sensitivity based on its partial arrest in response to IPTG.

TABLE III

| Line | $G_1/G_2$ (-IPTG) | $G_0/G_1$ (+IPTG) |
|---|---|---|
| POP | 2.6 | 2.7 |
| POP/p16 | 3.5 | 45.0 |
| rev1 | 3.5 | 6.6 |
| rev2 | 2.2 | 3.1 |
| rev3 | 3.6 | 4.0 |
| rev4 | 1.9 | 1.2 |
| rev5 | 3.8 | 4.4 |
| rev6 | 1.7 | 1.8 |

Figure 4:
FIG. 4 depicts expression of p16 in the revertant cell lines derived from HS294T/p16$^+$ cells.
Figure 4:
Figure 4:
Figure 5:
FIG. 5 depicts expression of Rb in the revertant cell lines derived from HS294T/p16$^+$ cells.
Figure 5:

The expression status of the p16, Rb, and CDK4 gene products was examined in the revertant line by western blot analysis. See, FIGS. 4 and 5. Four of the six lines had lost expression of the inducible p16 construct. A fifth line had no detectable Rb protein, while a sixth line, rev6, appeared to have the expected levels of p16, Rb, CDK4 and cyclinD1.

Flow Cytometry. Revertant and control cell lines were grown to about 70% confluency and treated with 0.1 mM IPTG for twenty four (24) hours. The cells were immediately harvested, fixed in ethanol, and stained with propidium iodide prior to analysis on a FACscan flow cytometer (Becton-Dickinson). Estimates of cells in $G_1$ and $G_2$ were made by fitting Gaussian curves to the fluorescence data and integrating the curves using the program (Modfit; Verity House Software).

Western Blots. The revertant and control cell lines were treated with 0.1 mM IPTG for twenty four (24) hours prior to making total cell lysates. $1 \times 10^7$ cells were washed and resuspended in lysate buffer (0.1 M NaCl, 0.01 M TrisCl pH 7.6, 1 mM EDTA pH 8.0), boiled, and frozen at $-80°$ C. Approximately equal amounts of thawed total protein were run on SDS polyacrylamide gels and transferred using the semi-dry method (Hoeffer) onto nitrocellulose membranes. Blocking and antibody treatment of the blots was according to standard procedures (BioRad). Primary antibodies were obtained from various sources: anti-p16, anti-CDK4, and anti-cyclin-D1 where obtained from the ICRF (London, UK); anti-RB was obtained from Santa Cruz Biotechnology (Santa Cruz, Calif.). The blotted proteins were visualized using alkaline phosphatase (BioRad).

D. Example 4
Selection Systems Based on Expression of the Retinoblastoma Gene Product In analogy to the p16-arrest experiments, the rb gene may be expressed in tumor cells to select for the identification of novel cell proliferation genes. The so obtained selection systems may be used for the selection of random revertants or for the isolation of revertants obtained upon induction with perturbagens. See, supra. Revertants of rearrested cells are expected contain alterations in a set of genes that overlaps considerably with the p16-arrested revertants because rb acts downstream in the same signal transduction pathway as p16.

Further analysis of the rb-revertants will reveal the identity of cell proliferation genes useful for the diagnosis, prognosis, and for the development of targeted drugs for the treatment of diseases related to unregulated or inappropriate cell proliferation related to the rb signal transduction pathway.

E. Example 5
Selection Systems Based on the Expression of Genes in the P53 and the P21 Pathway Selection systems are designed which involve the p53/p21 pathway. p53 or p21 are employed in selection experiments analogous to the p16-arrest experiments described in Example 1, supra, to select for random revertants or for the isolation of revertants obtained upon induction with perturbagens.

Further analysis of the p53 or p21 revertants will reveal the identity of cell proliferation genes useful for the diagnosis, prognosis and for the development of targeted drugs for the treatment of diseases related to unregulated or inappropriate cell proliferation associated with the p53 or p21 pathway.

F. Example 6
Selection Systems Based on Expression of the BRCA1 Gene

In analogy to the p16-arrest experiments, the BRCA1 gene may be expressed in tumor cell lines to select for the identification of novel cell proliferation genes. Specifically, BRCA1 is overexpressed in the breast cancer cell line MCF-7. The so obtained selection systems may be used for the selection of random revertants or for the isolation of revertants obtained upon induction with perturbagens.

Revertants of BRCA1-arrested cells are analyzed to identify downstream mediators of BRCA1 tumor suppressor function, which may be useful for diagnosis, prognosis, and the development of drugs for the treatment of diseases related to unregulated or inappropriate cell proliferation associated with BRCA1, such as breast cancer.

G. Example 7
Selection Systems Based on Expression of CDK Inhibitors

CDK inhibitors, including p15, p16, p18, p21, p27, p57 are expressed in Rb+ cells to select for random revertants or for the isolation of revertants obtained upon induction with perturbagens.

Revertants of the CDK inhibitor-based selection systems are isolated and analyzed to identify upstream mediators of CDK inhibitors; the information obtained will be useful for the diagnosis, prognosis and for the development of targeted drugs for the treatment of diseases related to unregulated or inappropriate cell proliferation associated with CDK inhibitors.

H. Example 8
Selection Systems Based on Components of Oncogene Pathways

In order to identify the components of oncogene pathways, dominant-negative oncogenes or oncogene fragments of interest are expressed ectopically in a transformed cell such that growth is inhibited or apoptosis is induced. The dominant-negative oncogenes and cell systems employed in this experiment are listed in TABLE I, supra. The transformed cell lines may be used for the selection of random revertants or for the isolation of revertants obtained upon induction with perturbagens.

Revertant cells are isolated and analyzed to identify altered proliferation genes downstream in the oncogene's growth control pathway. These proliferation genes may be useful for the diagnosis, prognosis and for the development of targeted drugs for the treatment of diseases related to unregulated or inappropriate cell proliferation associated with oncogenes.

I. Example 9
Selection Systems Based on Tumor Formation and Metastasis In Vivo Genes that render tumorigenic cells non-tumorigenic are overexpressed in tumor cell lines. The non-tumorigenic cells are injected into immuno-compromised mice, e.g., nude mice, followed by the isolation of clonal tumor variants. Revertant cell lines may be induced by introduction of perturbagens.

Analysis of these revertant cells permits the isolation of important cell proliferation genes that contribute to tumor formation, and genes that contribute to tumor formation in vivo may be directly analyzed and recovered. The so obtained genes may be used for the diagnosis, prognosis, and for the development of targeted drugs for the treatment of diseases related to unregulated or inappropriate cell proliferation associated with aberrant expression or control of these cell proliferation genes.

J. Example 10
Selection Systems Based on Apoptosis

Lymphocytes or cells derived from a lymphocyte cell line are cultured in tissue culture flasks to subconfluence. Anti-FAS antibody is added to the media in order to stimulate the FAS receptor, resulting in the induction of apoptosis; surviving revertant cells that fail to die are then isolated. These survivors which have lost, by mutation, key functions in the apoptotic pathway under study are identified and analyzed and the underlying genes responsible for apoptosis or loss of apoptsis recovered. Revertants may also be induced by the introduction of perturbagens.

Analysis of these revertant cells allow the isolation of cell proliferation genes that are involved in apoptopic pathways, which may be useful for the diagnosis, prognosis and treatment of diseases related to unregulated or inappropriate cell proliferation.

K. Example 11
Selection Systems Based on Contact Inhibition

A human melanoma cell line which generally is contact inhibited, such as HT-144, is grown in tissue culture flasks. Non-contact inhibited revertant cells that have lost important growth regulatory signals are identified by the formation of foci or their ability to grow in soft agar and isolated.

Revertants may also be induced by the introduction of perturbagens. Gene expression is compared with that of the non-revertant parent cell line, and differentially expressed genes in the revertant-cells are identified and recovered. The so obtained genes may be used, e.g., for diagnosis, prognosis and the development of targeted drugs for the treatment of, e.g., cancer, in particular the treatment of melanoma.

L. Example 12
Selection Systems Based on the Growth Factor Requirement of Non-Transformed Cells Non-transformed cells such as melanocytes are cultured in tissue culture flasks in culture medium supplemented with all required factors, including phorbol ester, FGF, MSH-A, insulin/IGF-1. When the cells are semiconfluent, a selected growth factor is removed from the media, resulting in death of the vast majority of cells. Subsequently, revertant cells which continue to grow in the absence of the factor are selected.

Reversion of the cells may also be induced by introduction of perturbagens. The mutations that have eliminated the function of the regulatory pathway that prevents growth in the absence of the factor are identified and the corresponding genes recovered. The so obtained genes can have numerous medical applications, including diagnosis and prognosis of diseases related to uncontrolled cell proliferation, and the development of drugs for the treatment of such diseases.

M. Example 13
Selection Systems Based on the Inability of Non-Transformed T-Cells to Grow in Isolation Many non-transformed T-cell lines can only be cloned, i.e., grown in isolation from other neighbors when the individual cells are placed on a "feeder layer" of other cells.

Non transformed T cell lines are diluted to a concentration of 100 cells/ml; 10 ml of this cell suspension are then seeded on a ten (10) cm tissue culture plate. Revertants cells which do grow at low density in colonies are selected. Such revertants are presumed to contain alterations in genes involved in a pathway of growth dependence on neighbors, and hence, depend on secreted factors. Revertant cells are selected and isolated, and the corresponding genes are recovered. The so identified cell proliferation genes may be used, e.g., for diagnosis, prognosis, and the development of targeted drugs for cancer therapy.

N. Example 14

Selection Systems Based on Immortalization of Primary Cells

Freshly isolated human primary epithelial cells are cultured in suitable media; the vast majority of the cells has a finite lifespan and die after a certain number of cell doublings. Revertants which survive the "crisis phase" are selected. These revertant cells have undergone changes that lead to immortalization and contain for mutations in genes that normally limit life span. Subsequently, the differentially expressed or initiated genes from these revertant cells when compared to normal primary cells are recovered.

All references cited within the body of the instant specification are hereby incorporated by reference in their entirety.

What is claimed is:

1. A process for identifying a cell proliferation gene comprising the steps of:
   (a) selecting a growth proficient revertant cell from a plurality of cultured cells arrested for growth, said growth arrested cells transformed with a library comprising a plurality of nucleic acid sequence inserts, wherein at least one insert from the library encodes a perturbagen within said reverent cell, said perturbagen selected from the group consisting of a DNA encoding a cell proliferation gene, an RNA which can bind to an endogenous cell component, a peptide which can complement or interfere with an endogenous protein/protein interaction, and a DNA which encodes said RNA or peptide, wherein said perturbagen induces said reversion to growth proficiency by complementing or disrupting the function of an unspecified component in an endogenous growth control pathway; and
   (b) identifying one or more genes or gene products in said revertant cell that cause said reversion to growth proficiency.

2. The process of claim 1 wherein growth arrest of the cultured cells is caused by expression of a tumor suppressor gene or a dominant negative oncogene.

3. The process of claim 1 wherein growth arrest of said cultured cells is caused by the expression of a gene inducing apoptosis in said cells.

4. The process of claim 3 wherein said gene is expressed under the control of an inducible promoter.

5. The process of claim 2 wherein said gene is a tumor suppressor gene selected from the group consisting of P16, P53, RB1, WT1, BRCA1, BRCA2, NF1, NF2, P15, P18, P19, P21, P27, P57 and VHL.

6. The process of claim 5 wherein the tumor suppressor gene is p16.

7. The process of claim 1 wherein the cultured cells are selected from the group consisting of cells derived from primary tumors, cells derived from metastatic tumors, primary cells, cells which have lost contact inhibition, transformed primary cells, immortalized primary cells, cells which may undergo apoptosis, and cell lines derived therefrom.

8. The process of claim 7 wherein the cultured cells express rb.

9. The process of claim 7 wherein the cultured cells are derived from a melanoma cell line.

10. The process of claim 9 wherein the melanoma cell line is HS294T.

11. The process of claim 4 wherein the inducible promoter is an IPTG inducible promoter.

12. The process of claim 2 or 3, wherein said gene has been introduced on an expression plasmid under the control of a promoter.

13. The process of claim 1, further comprising the steps of:
   (a) measuring differences in gene expression between said revertant cells and said growth arrested cultured cells to identify differentially expressed genes; and
   (b) isolating genes identified in step (a) to identify a differentially expressed cell proliferation gene.

14. The process of claim 1 wherein the perturbagen is DNA encoding an RNA or polypeptide product which upon expression confers growth proficiency on said revertant cells.

15. The process of claim 14, further comprising the steps of:
   (a) isolating the perturbagen present in said revertant cells; and
   (b) identifying the sequence of said perturbagen.

16. The process of claim 1, wherein the perturbagen is DNA encoding a cell proliferation gene, a gene product thereof, or an active fragment of said gene or gene product.

17. The process of claim 1, further comprising the step of identifying at least one cell component which interacts with said perturbagen to cause said reversion to growth proficiency.

18. The process of claim 17 wherein said cell component is selected from the group consisting of a cell proliferation gene and a gene product thereof.

19. The process of claim 1 wherein the perturbagen is or encodes a dominantly active peptide that complements or disrupts an endogenous growth control pathway.

20. The process of claim 1 wherein the perturbagen library is introduced into said cells using a retroviral vector.

21. The process of claim 19 wherein the perturbagen disrupts the action of a cellular tumor suppressor gene, or its downstream target(s), said process further comprising:
   (a) identifying said tumor suppressor gene; and
   (b) isolating said tumor suppressor gene.

22. The process of claim 19 wherein the perturbagen disrupts the action of a cellular proto-oncogene, or its downstream target(s), said process further comprising:
   (a) identifying said cellular oncogene; and
   (b) isolating said cellular oncogene.

23. A method to identify expression in a tissue sample of a cell proliferation gene identified by the process of claim 1, 13–18, 21 or 22, comprising the steps of:
   (a) exposing nucleic acid derived from mRNA of said tissue sample to a labeled oligonucleotide probe comprising a sequence complementary to a fragment of said cell proliferation gene; and
   (b) identifying specific hybridization of said oligonucleotide probe with said nucleic acid.

24. A method to identify an individual predisposed to cancer comprising the steps of:
   (a) exposing nucleic acid derived from chromosomal DNA from said individual to a labeled oligonucleotide probe comprising a sequence complementary to a fragment of a cell proliferation gene, said cell proliferation gene identified according to the process of claims 1 or 14; and (b) identifying specific hybridization of said probe with said nucleic acid.

25. The process of claim 2, wherein the gene is a dominant negative oncogene selected from the group consisting of cJUN, EGF-R, GRB2, RAF, MAX, RAS, SRC, and tyrosine kinase receptor mutants.

26. The process of claim 14, wherein the one or more perturbagens comprise a nucleic acid which encodes an RNA or polypeptide expression product that confers growth proficiency on said revertant cells.

27. The process of claim 1 wherein the cell proliferation gene is selected from the group consisting of an oncogene, a dominant transforming gene, a tumor suppressor gene and a gene involved in the control of apoptosis.

28. The process of claim 19 wherein the endogenous gene is a tumor suppressor gene or a dominant-negative proto-oncogene.

* * * * *